United States Patent
Kimura et al.

(10) Patent No.: US 10,101,282 B2
(45) Date of Patent: Oct. 16, 2018

(54) SCATTERING TOMOGRAPHY METHOD AND SCATTERING TOMOGRAPHY DEVICE

(71) Applicants: National University Corporation Kobe University, Hyogo (JP); Integral Geometry Science Inc., Hyogo (JP)

(72) Inventors: Kenjiro Kimura, Hyogo (JP); Noriaki Kimura, Hyogo (JP)

(73) Assignees: NATIONAL UNIVERSITY CORPORATION KOBE UNIVERSITY, Hyogo (JP); INTEGRAL GEOMETRY SCIENCE INC., Hyogo (JP)

( * ) Notice: Subject to any disclaimer, the term of this patent is extended or adjusted under 35 U.S.C. 154(b) by 220 days.

(21) Appl. No.: 15/262,448

(22) Filed: Sep. 12, 2016

(65) Prior Publication Data
US 2016/0377557 A1    Dec. 29, 2016

Related U.S. Application Data

(63) Continuation of application No. PCT/JP2015/001353, filed on Mar. 11, 2015.

(30) Foreign Application Priority Data

Mar. 12, 2014  (JP) ................................. 2014-049536
Mar. 12, 2014  (JP) ................................. 2014-049551

(51) Int. Cl.
*G01R 27/04*   (2006.01)
*G01N 22/00*   (2006.01)
(Continued)

(52) U.S. Cl.
CPC ............. *G01N 22/00* (2013.01); *G01N 22/02* (2013.01); *G06T 11/003* (2013.01)

(58) Field of Classification Search
CPC ........ G01R 27/06; G01R 27/28; G01R 31/11; G01N 22/00
See application file for complete search history.

(56) References Cited

U.S. PATENT DOCUMENTS 4,805,627 A    2/1989   Klingenbeck et al.
5,363,050 A    11/1994  Guo et al.
(Continued)

FOREIGN PATENT DOCUMENTS

DE    10 2009 00725    12/2009
JP    62-66145         3/1987
(Continued)

OTHER PUBLICATIONS

Extended European Search Report dated Sep. 27, 2017 in corresponding European patent application No. 15 75 0923.
(Continued)

*Primary Examiner* — Tung X Nguyen
(74) *Attorney, Agent, or Firm* — Wenderoth, Lind & Ponack, L.L.P.

(57) ABSTRACT

A scattering tomography method includes: radiating waves to an object from a plurality of transmitting antenna elements aligned on a side surface of a case; receiving scattered waves by a plurality of receiving antenna elements aligned on the side surface of the case; and reconstructing an image relating to information on an interior of the object using scattered wave data representing the scattered waves. In the reconstructing, a reconstruction function for reconstructing the image relating to the information on the interior of the object is set in advance for a three-dimensional space having the same shape as the case, a scattering field equation which the reconstruction function satisfies is constructed, a visualization function that is obtained by solving the scattering field equation is derived from the scattered wave data, and the image relating to the information on the interior of the object is reconstructed using the visualization function.

15 Claims, 10 Drawing Sheets

(51) Int. Cl.
   *G01N 22/02* (2006.01)
   *G06T 11/00* (2006.01)

(56) References Cited

U.S. PATENT DOCUMENTS

| | | | |
|---|---|---|---|
| 5,588,032 | A | 12/1996 | Johnson et al. |
| 5,715,819 | A | 2/1998 | Svenson et al. |
| 5,810,010 | A | 9/1998 | Anbar |
| 5,961,466 | A | 10/1999 | Anbar |
| 5,999,843 | A | 12/1999 | Anbar |
| 6,035,225 | A | 3/2000 | Anbar |
| 6,253,100 | B1 | 6/2001 | Zhdanov |
| 6,873,569 | B2 | 3/2005 | Vernet et al. |
| 6,876,878 | B2 | 4/2005 | Zhdanov |
| 7,265,717 | B2 | 9/2007 | Saitou et al. |
| 7,292,719 | B2 | 11/2007 | Arnon |
| 7,550,969 | B2 | 6/2009 | Zhdanov |
| 8,116,845 | B2 | 2/2012 | Hashimshony et al. |
| 8,400,166 | B2 * | 3/2013 | Geren .................. G01R 27/00 324/637 |
| 8,583,393 | B2 | 11/2013 | Kitazawa et al. |
| 8,721,565 | B2 | 5/2014 | Hashimshony et al. |
| 8,738,124 | B2 | 5/2014 | Davies |
| 8,838,405 | B2 | 9/2014 | Kitazawa et al. |
| 8,864,669 | B2 | 10/2014 | Behar |
| 8,870,772 | B2 | 10/2014 | Behar |
| 8,882,672 | B2 | 11/2014 | Behar |
| 9,164,033 | B2 | 10/2015 | Edwards et al. |
| 2002/0062074 | A1 | 5/2002 | Zhdanov |
| 2004/0004906 | A1 | 1/2004 | Vernet et al. |
| 2005/0088344 | A1 | 4/2005 | Saitou et al. |
| 2006/0237652 | A1 * | 10/2006 | Kimchy .................. A61B 1/05 250/363.02 |
| 2007/0032739 | A1 | 2/2007 | Hashimshony et al. |
| 2007/0032747 | A1 | 2/2007 | Hashimshony et al. |
| 2007/0060816 | A1 | 3/2007 | Simpkin |
| 2007/0073144 | A1 | 3/2007 | Simpkin |
| 2007/0093708 | A1 | 4/2007 | Benaron et al. |
| 2007/0110293 | A1 | 5/2007 | Arnon |
| 2007/0230767 | A1 | 10/2007 | Iwamatsu et al. |
| 2007/0293752 | A1 | 12/2007 | Simpkin |
| 2008/0071169 | A1 | 3/2008 | Craddock et al. |
| 2009/0012391 | A9 | 1/2009 | Simpkin |
| 2009/0024026 | A9 | 1/2009 | Simpkin |
| 2009/0119040 | A1 | 5/2009 | Zhdanov |
| 2009/0171236 | A1 | 7/2009 | Davies |
| 2009/0293621 | A1 | 12/2009 | Kitazawa et al. |
| 2011/0087096 | A1 | 4/2011 | Behar |
| 2011/0087097 | A1 | 4/2011 | Behar |
| 2011/0237956 | A1 | 9/2011 | Edwards et al. |
| 2012/0083683 | A1 | 4/2012 | Kuwabara |
| 2012/0137778 | A1 | 6/2012 | Kitazawa et al. |
| 2012/0316439 | A1 | 12/2012 | Behar |
| 2014/0035911 | A1 | 2/2014 | Kitazawa et al. |
| 2014/0357998 | A1 | 12/2014 | Suzuki et al. |
| 2015/0377778 | A1 | 12/2015 | Kimura et al. |

FOREIGN PATENT DOCUMENTS

| | | |
|---|---|---|
| JP | 8-054379 | 2/1996 |
| JP | 8-54379 | 2/1996 |
| JP | 8-304538 | 11/1996 |
| JP | 10-504893 | 5/1998 |
| JP | 2002-512070 | 4/2002 |
| JP | 2003-177656 | 6/2003 |
| JP | 2004-512117 | 4/2004 |
| JP | 2004-141447 | 5/2004 |
| JP | 2005-130292 | 5/2005 |
| JP | 2006-279526 | 10/2006 |
| JP | 2007-61359 | 3/2007 |
| JP | 2008-505684 | 2/2008 |
| JP | 2008-512175 | 4/2008 |
| JP | 4176613 | 11/2008 |
| JP | 2009-508539 | 3/2009 |
| JP | 2009-512500 | 3/2009 |
| JP | 2009-276319 | 11/2009 |
| JP | 2009-288129 | 12/2009 |
| JP | 2010-69158 | 4/2010 |
| JP | 2010-230466 | 10/2010 |
| JP | 4558553 | 10/2010 |
| JP | 2011-505966 | 3/2011 |
| JP | 2012-505398 | 3/2012 |
| JP | 2013-29527 | 2/2013 |
| JP | 2013-31668 | 2/2013 |
| JP | 2013-515586 | 5/2013 |
| JP | 2013-116214 | 6/2013 |
| WO | 95/32665 | 12/1995 |
| WO | 99/53840 | 10/1999 |
| WO | 2004/061575 | 7/2004 |
| WO | 2006/003658 | 1/2006 |
| WO | 2006/006559 | 1/2006 |
| WO | 2006/028395 | 3/2006 |
| WO | 2007/015255 | 2/2007 |
| WO | 2007/046983 | 4/2007 |
| WO | 2009/082434 | 7/2009 |
| WO | 2009/146881 | 12/2009 |
| WO | 2010/043851 | 4/2010 |
| WO | 2010/143691 | 12/2010 |
| WO | 2011/080712 | 7/2011 |
| WO | 2014/125815 | 8/2014 |

OTHER PUBLICATIONS

International Search Report (ISR) dated May 20, 2014 in International (PCT) Application No. PCT/JP2014/000722.

Extended European Search Report dated Oct. 28, 2015 in corresponding European Patent Application No. 14751867.4.

Kazuaki Ezawa et al., "Development of the 3D Imaging Radar for Inspection of Tunnel Lining Concrete", Mitsui ZousenGiho, No. 184, p. 24, Feb. 2005, together with English abstract.

Matthew J. Burfeindt et al., "Quantitative Microwave Imaging of Realistic Numerical Breast Phantoms Using an Enclosed Array of Multiband, Miniaturized Patch Antennas", IEEE Antennas and Wireless Propagation Letters, vol. 11, 2012, pp. 1626-1629.

Kazuyuki Nakahata et al., "Development of flaw shape imaging method using ultrasonic linear array transducer", The Japan Society of Mechanical Engineers, JSME annual meeting 2005(1), pp. 679-680, Sep. 2005, together with English abstract.

Kazuyuki Nakahata et al., "Ultrasonic Imaging of Internal Flaw with Flexible Array Transducer Located on Irregular Surface", The Institute of Electronics, Information and Communication Engineers, IEICE Technical Report, Jun. 2012, together with English abstract.

Kenjiro Kimura et al., "Development of high-resolution magnetic imaging method with tunneling magnetoresistance device for inspecting reinforcing steels inside concrete building", The Japanese Society for Non-Destructive Inspection KoenTaikai Koen Gaiyoshu, Heisei 24 Nendo Shunki,, The Japanese Society for Non-Destructive Inspection, pp. 89-92, May 22, 2012, together with English partial translation.

Natterer, F., "Imaging and Inverse Problems of Partial Differential Equations," 2006, pp. 1-22.

Semenov, Serguei, "Microwave tomography: review of the progress towards clinical applications," Phil. Trans. R. Soc. A, 2009, pp. 3021-3042, XP-002661164.

Kenjiro Kimura et al., "Developments of Electromagnetic Field Reconstruction Method and Scanning Tunneling Magnetoresistance Microscope," Electronic Packaging Technology, Jan. 20, 2012, vol. 28, No. 2, p. 16-20—with partial English translation (p. 16, left column, lines 1 to 27—right column, lines 1 to 8).

Yuki Mima et al., "Improvement of spatial resolution of magnetic imaging with Radon transform," Dai 73 Ouyou Butsuri Gakkai Gakujyutsu Kouenkai Kouen Youkoushu, Aug. 27, 2012. vol. 73rd, p. 01-117. ROMBUNNO.11A-C10-7—with partial English translation (p. 01-117, lines 1 to 19, and explanation of Fig.1).

Yuki Mima et al., "Development of tunneling magnetoresistance microscope with electromagnetic field reconstruction and its application to visualizing electric current inside battery," The 54th Battery Symposium in Japan, Oct. 7-9, 2013, Osaka, p. 423—with English abstract.

(56) References Cited

OTHER PUBLICATIONS

Kenjiro Kimura et al., "Development of High-resolution Magnetic Imaging Method with Tunneling Magnetoresistance Device to Inspect Reinforcing Steels Inside a Concrete Building," Journal of the Japanese Society for Non-destructive Inspection, Oct. 2013, pp. 527-528—with partial English translation (p. 527, left column, lines 1 to 26—right column, lines 1 to 13).

Nozomu Okada et al., "Investigation of microwave CT antenna by TLM method," 2000 Year Denshi Jyouhou Tsuushin Gakkai Sougou Taikai, Mar. 7, 2000, vol. 2000, Sougou 6, p.104—with partial English translation (p. 104, left column, lines 1 to 12).

Masashi Takabayashi et al., "High speed imaging of microwave CT using an antenna array based on the modulation scattering,"Denki Gakkai Iyou • Seitai Kougaku Kennkyuukai Shiryou, Mar. 8, 2000, vol. MBE-00, No. 1-14, pp. 47-51—with English abstract.

S. Caorsi et al., "A multiview microwave imaging system for two-dimensional penetrable objects," IEEE Trans Microw Theory Tech, May 1991. pp. 845-851, vol. 39, No. 5.

Shantanu Padhi et al., "A PC-controlled microwave tomographic scanner for breast imaging," Rev Sci Instrum, Jan. 2011, p. 014702, vol. 82, No. 1.

Osamu Kanno et al., "High speed measurement of the microwave thermal CT by use of the antenna array," Denshi Jyouhou Tsuushin Gakkai Taikai Kouen Ronbunshu, Mar. 1995, p. 211, vol. 1995, No. Sogo Pt 6—with partial English translation (p. 211, left column, lines 1 to 6).

Masashi Takabayashi et al., "A chirp radar-type microwave CT—A high-speed imaging by modulation scattering method," Denshi Jyouhou Tsuushin Gakkai Taikai Kouen Ronbunshu, Mar. 1997, p. 168, vol. 1997, No. Sogo Pt 6—with partial English translation (p. 168, left column, lines 1 to 15).

Yuki Mima et al., "Investigation of current density distribution inside battery by tunneling magnetoresistance microscopy with electromagnetic field reconstruction method," The 53rd Battery Symposium in Japan, Nov. 14-16, 2012, Fukuoka, p. 54—with English abstract.

Japanese Office Action dated Aug. 21, 2018 in corresponding Japanese Patent Application No. 2016-507364 with partial English translation.

Takashi Takenaka, "Inverse Scattering Analysis Based on Optimization Techniques", Proceedings of the 2011 IEICE Electronics Society Conference 1, Japan, The Institute of Electronics, Information and Communication Engineers, 2011, S1-2.

* cited by examiner

SCATTERING TOMOGRAPHY METHOD AND SCATTERING TOMOGRAPHY DEVICE

CROSS REFERENCE TO RELATED APPLICATIONS

This is a continuation application of PCT International Application No. PCT/JP2015/001353 filed on Mar. 11, 2015, designating the United States of America, which is based on and claims priority of Japanese Patent Applications No. 2014-049536 filed on Mar. 12, 2014 and No. 2014-049551 filed on Mar. 12, 2014. The entire disclosures of the above-identified applications, including the specifications, drawings and claims are incorporated herein by reference in their entirety.

FIELD

The present invention relates to technology for obtaining and visualizing (imaging) information on the interior of an object using waves, and particularly to a scattering tomography method and a scattering, tomography device in which a wave scattering phenomenon is used.

BACKGROUND

Conventionally, x-ray computed tomography (CT) (x-ray tomography), magnetic resonance imaging (MRI), positron emission tomography (PET), and other methods are used to visualize information on the interior of an object such as a living body and a building. Specifically, electromagnetic waves such as light, terahertz waves, millimeter waves, and microwaves, or waves such as ultrasonic waves, sound waves, and elastic waves are radiated to a living body or an object that is to be observed, or are radiated to plasma, and resultant scattered waves (reflected waves) are observed and analyzed to visualize information on the interior of the living body, the interior of the solid object, or the interior of the plasma. Recently, instead of waves, a static electromagnetic field or a quasi-static electromagnetic field is also used to visualize information on the interior of a living body or an object.

Generally, these methods use a technique in which waves u such as electromagnetic waves or ultrasonic waves are radiated to an object O, scattered waves p that are waves scattered by the object O are observed at multiple places around the object O, and resultant data is visualized (for example, refer to Patent Literature (PTL) 1 and Non Patent Literature (NPL) 1).

In the technique disclosed in PTL 1, information on the interior of an object is visualized using radio waves. For the visualization, data on scattered waves observed with a sensor arranged on the circumference of a circle is repeatedly obtained while the data is modified using a parameter such as electrical conductivity or permittivity.

The technique disclosed in NPL 1 is a technique related to a multi-path linear array radar and allows information on a flaw or the like inside concrete to be visualized. In this technique, a linear sensor (a linear multi-array antenna) is arranged on a surface of an object to observe scattered waves of radiated waves, and observed data is analyzed and visualized.

CITATION LIST

Patent Literature

[PTL 1] Japanese Unexamined Patent Application Publication No. 2003-177656

Non Patent Literature

[NPL 1] Development of the 3D Imaging Radar for Inspection of Tunnel Lining Concrete, MITSUI ZOSEN TECHNICAL REVIEW No. 184 (2005-2), p. 24

SUMMARY

Technical Problem

With the techniques disclosed in PTL 1 and NPL 1, every time the conditions including the curved shape of an object change, for example, it is necessary to reload data or modify obtained data by using a different theory or with a different internal device structure; thus, versatile use of these techniques is less likely. In particular, the conventional linear multi-array antennas are difficult to use in a versatile manner for an object having a flexible shape, such as a living body, because the shape or the curvature of an outer curved surface of the object is often not constant. In addition, there are also problems of a low calculation speed and high memory usage due to the need for data reload or modification.

Thus, an object of the present invention is to provide a versatile scattering tomography method and a scattering tomography device by which information on the interior of an object can be visualized easily at high speed and with high precision.

Solution to Problem

In order to solve the above-described problems, a scattering tomography method according to one aspect of the present invention is a scattering tomography method for analyzing scattered waves of waves radiated to an object placed in a case, and includes: radiating the waves to the object from a plurality of transmitting antenna elements aligned on a side surface of the case in a same direction as an axis of rotational symmetry of the case when seen in a plan view; receiving the scattered waves by a plurality of receiving antenna elements aligned on the side surface of the case in the same direction as the axis of rotational symmetry of the case when seen in a plan view; and reconstructing an image relating to information on an interior of the object using scattered wave data representing the scattered waves received by the plurality of receiving antenna elements, wherein in the reconstructing: a reconstruction function for reconstructing the image relating to the information on the interior of the object is set in advance for a three-dimensional space having a same shape as the case; a scattering field equation which the reconstruction function satisfies is constructed; a visualization function that is obtained by solving the scattering field equation is derived from the scattered wave data; and the image relating to the information on the interior of the object is reconstructed using the visualization function.

With this, a partial differential equation for the inverse problem is set in an analysis model in which a sensor is arranged on the side surface of the case, and solving this equation allows information on the interior of an object placed in the case to be visualized at high speed in a versatile manner. Furthermore, since the reconstruction function Φ is set for a three-dimensional space in the reconstructing, information on the interior of an object can be more accurately visualized in three dimensions at high speed.

Furthermore, the case may be in the shape of a cone, and the plurality of transmitting antenna elements and the plurality of receiving antenna elements may be arranged along a generatrix of the cone of the case.

With this, a partial differential equation for the inverse problem is set in an analysis model in which a sensor is arranged on the generatrix of the cone on the side surface of the case, and solving this equation allows information on the interior of an object to be visualized at high speed and with high precision in a versatile manner. In particular, information on the interior of a conical object can be more accurately visualized at high speed.

Furthermore, the case may be in the shape of a substantial cone having a curved generatrix, and the plurality of transmitting antenna elements and the plurality of receiving antenna elements may be arranged along the curved generatrix.

With this, a partial differential equation for the inverse problem is set in an analysis model in which a sensor is arranged on the curved generatrix on the side surface of the case, and solving this equation allows information on the interior of an object to be visualized at high speed and with high precision in a versatile manner. In particular, information on the interior of a substantially conical object including a semispherical or dome-shaped object, for example, can be more accurately visualized at high speed.

Furthermore, the waves may be microwaves.

With this, even information on the interior of an object having a high water content can be visualized precisely in a versatile manner.

Furthermore, the waves may be pulsed waves or periodic waves having a predetermined frequency.

With this, information on the interior of an object having a flexible shape can be visualized precisely in a versatile manner.

In order to solve the above-described problems, a scattering tomography device according to one aspect of the present invention is a scattering tomography device for analyzing scattered waves of waves radiated to an object placed in a case, and includes: a plurality of transmitting antenna elements that are aligned on a side surface of the case in a same direction as an axis of rotational symmetry of the case when seen in a plan view, and radiate the waves to the object; a plurality of receiving antenna elements that are aligned on the side surface of the case in the same direction as the axis of rotational symmetry of the case when seen in a plan view, and receive the scattered waves that are the waves radiated to the object and scattered in the object; and an image reconstructor that reconstructs an image relating to information on an interior of the object using scattered wave data representing the scattered waves received by the plurality of receiving antenna elements, wherein the image reconstructor: sets in advance a reconstruction function for reconstructing the image relating to the information on the interior of the object, for a three-dimensional space having a same shape as the case; constructs a scattering field equation which the reconstruction function satisfies; derives, from the scattered wave data, a visualization function that is obtained by solving the scattering field equation; and reconstructs, using the visualization function, the image relating to the information on the interior of the object.

With this, a partial differential equation for the inverse problem is set in an analysis model in which a sensor is arranged on a side surface of the case, and solving this equation allows information on the interior of an object placed in the case to be visualized at high speed and with high precision in a versatile manner. Furthermore, since the reconstruction function φ is set for a three-dimensional space in the reconstructing, information on the interior of an object can be more accurately visualized in three dimensions at high speed.

Furthermore, each of the plurality of transmitting antenna elements may include a first wideband antenna including: a first active balanced circuit that has two input terminals and two output terminals and includes a semiconductor element; a first antenna element connected to one of the two output terminals; a second antenna element connected to a remaining one of the two output terminals; and a first resistance element that causes each of the first antenna element and the second antenna element to be grounded, and each of the plurality of receiving antenna elements includes (i) a second wideband antenna including: a second active balanced circuit that has two input terminals and two output terminals and includes a semiconductor element; a third antenna element connected to one of the two input terminals; a fourth antenna element connected to a remaining one of the two input terminals; a second resistance element that causes each of the third antenna element and the fourth antenna element to be grounded, and (ii) a mixer that converts a frequency of a received frequency signal.

With this, since a balun including a coil-type transformer is not used for an ultrawideband antenna, it is possible to provide high-speed, accurate mammography equipment.

Furthermore, the case may be in the shape of a cone, and the plurality of transmitting antenna elements and the plurality of receiving antenna elements may be arranged along a generatrix of the cone of the case.

With this, a partial differential equation for the inverse problem is set in an analysis model in which a sensor is arranged on the generatrix of the cone on the side surface of the case, and solving this equation allows information on the interior of an object to be visualized at high speed in a versatile manner. In particular, information on the inside of a conical object can be more accurately visualized at high speed.

Furthermore, the case may be in the shape of a substantial cone having a curved generatrix, and the plurality of transmitting antenna elements and the plurality of receiving antenna elements may be arranged along the curved generatrix.

With this, a partial differential equation for the inverse problem is set in an analysis model in which a sensor is arranged on the curved generatrix on the side surface of the case, and solving this equation allows information on the interior of an object to be visualized at high speed and with high precision in a versatile manner. In particular, information on the interior of a substantially conical object including a semispherical or dome-shaped object, for example, can be more accurately visualized at high speed.

Furthermore, the waves may be microwaves.

With this, even information on the interior of an object having a high water content can be visualized precisely in a versatile manner.

Furthermore, the waves may be pulsed waves or periodic waves having a predetermined frequency.

With this, information on the interior of an object having a flexible shape can be visualized precisely in a versatile manner.

Advantageous Effects

According to the present invention, the inverse problem is analyzed at high speed and with high precision in a versatile manner so that information on the interior of an object having a flexible shape can be visualized easily. And information on the interior of an object having a flexible shape can be more accurately visualized at high speed.

BRIEF DESCRIPTION OF DRAWINGS

These and other objects, advantages and features of the invention will become apparent from the following description thereof taken in conjunction with the accompanying drawings that illustrate a specific embodiment of the present invention.

DESCRIPTION OF EMBODIMENTS

Figure 1:
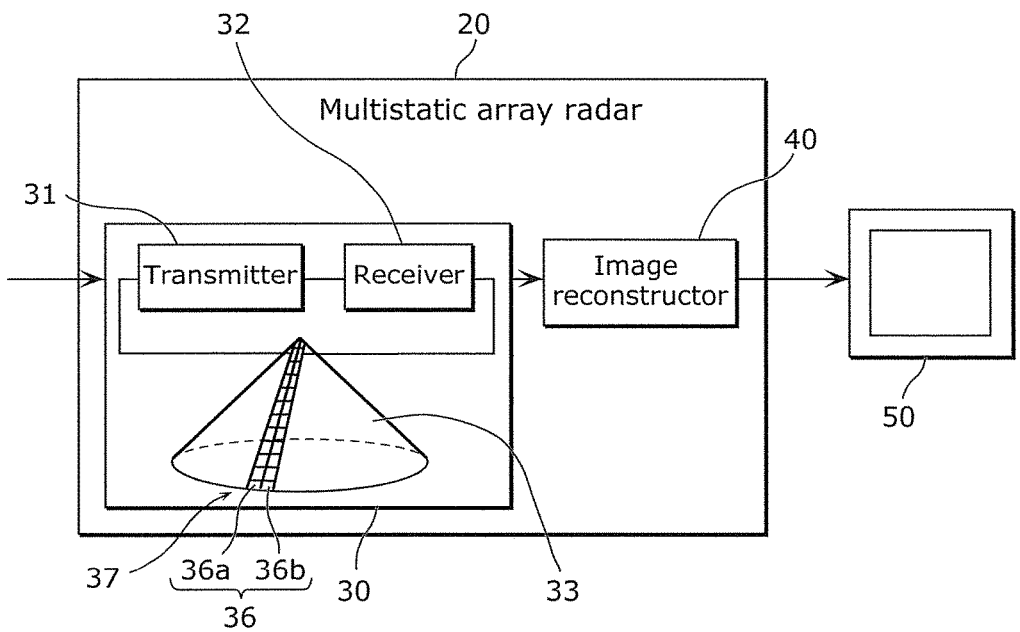
FIG. 1 schematically illustrates a configuration of a multistatic array radar according to Embodiment 1.

Underlying Knowledge Forming the Basis of the Present Invention

A technique forming the basis of the present invention is described below prior to describing embodiments of the present invention.

A scattering phenomenon occurring when waves are radiated to an object can be expressed using an operator. For example, using an operator A, a physics equation can be expressed as $p = A_u [O]$ where O is an object, u is radiated waves, and p is observed data. When the object O, the radiated waves u, and the operator (system function) A are known, the problem to solve the observed data p is called the forward problem. The forward problem is a mathematically well-established approach and can be solved with a method in a standard physics textbook.

On the other hand, an important issue in medical or industrial fields is a problem to solve what the object O is when the radiated waves u, the system function A, and the observed data p are known. This problem is called the inverse problem in the sense that the causal relation of a physical phenomenon is traced in an inverse direction, and can be expressed as $O = A_u^{-1} [p]$. This inverse problem is applied in a method of visualizing information on the interior of an object by observing and analyzing scattered waves when waves are radiated to the object (the scattering tomography).

The inverse problem is not a mathematically well-established approach—there has been no established theory for the inverse problem as of yet—unlike the forward problem, and thus is problematic not being easy to solve.

Furthermore, in order to visualize information on the interior of an object having a flexible shape, such as a living body, it is necessary to reload data or modify obtained data by using a different theory or with a different internal device structure every time the conditions including the curved shape of the object change, for example. For this reason, the method of visualizing information on the interior of an object using the inverse problem is difficult to use in a versatile manner. In addition, there are also problems of a low calculation speed and high memory usage due to the need for data reload or modification.

As an example of the above-described method of detecting a flaw or the like of an object using scattered waves of radiated waves in a non-destructive manner (the scattering tomography), a multistatic linear array radar is available. In this method, for example, antenna elements are attached as a sensor to an object, and even when the object has a curvature, the object is approximated by a plane, and a flaw or the like of the object is detected in a non-destructive manner based on the relationship between electromagnetic waves radiated from the antenna elements and reflected waves (scattered waves) that are the electromagnetic waves reflected in the object.

The multistatic linear array radar is used to detect a flaw or the like of an object in a non-destructive manner based on the relationship between radiated waves that are waves radiated to the object and reflected waves that are the radiated waves reflected in the object (scattered waves). A problem with the multistatic linear array radar is that depending on the shape of an object, specifically, a living body, the error that affects the phase of electromagnetic waves increases, resulting in an image obtained by calculation failing to be in focus.

Therefore, the following describes scattering tomography that can be used in a versatile manner even for an object having a flexible shape, such as a living body.

Hereinafter, embodiments of the present invention are described with reference to the Drawings. Note that the same or like structural elements share the same reference symbols in the Drawings.

Each of the following embodiments describes a specific preferred example of the present invention. The numerical values, shapes, materials, structural elements, the arrangement and connection of the structural elements, steps, the processing order of the steps etc., shown in the following embodiments are mere examples, and therefore do not limit the present invention. Therefore, among the structural elements in the following embodiments, structural elements not recited in any one of the independent claims which indicate the broadest concepts of the present invention are described as arbitrary structural elements in a more preferred embodiment.

Generally, the scattering tomography represents a method of detecting a flaw or the like of an object using scattered waves of radiated waves in a non-destructive manner. In order to clarify that the scattering tomography is a method, this method is hereinbelow referred to as a scattering tomography method. A device for performing the scattering tomography method is hereinbelow referred to as a scattering tomography device.

Embodiment 1

Configuration of Sensor Array

Embodiment 1 is described in which a one-dimensional sensor array is used as a sensor for performing the scattering tomography method. The one-dimensional sensor array includes a transmitting antenna element and a receiving antenna element arranged in one dimension (a curvilinear array antenna).

This embodiment describes a scattering tomography device for a conical model having a linear generatrix as an example of visualizing information on the interior of a living body, in particular, information on the position of a defective cell. Specifically, the substantially conical object is exemplified as a breast, and the defective cell is exemplified as a cancer cell in the breast.

In this device, the transmitting antenna element the receiving antenna element included in the curvilinear array antenna are arranged in a line along the generatrix of the conical body (in one dimension). The linear antenna is rotated for scanning in the circumferential direction of a circle that is the base of the cone.

First, a configuration of a multistatic array radar 20 which is a scattering tomography device according to this embodiment is described. The multistatic array radar 20 is a curvilinear array antenna in which a plurality of antenna elements for transmission are arranged in a line and a plurality of antenna elements for receiving are arranged in a line. In this curvilinear array antenna, an arbitrary element in the transmitting antenna element line transmits waves, and an arbitrary element in the receiving antenna element line receives reflected waves. For example, when $n_y$ transmitting antenna elements and $n_y$ receiving antenna elements are arranged in the y-axis direction, $n_y^2$ sets of time-series data items can be obtained.

FIG. 1 schematically illustrates a configuration of the multistatic array radar 20 according to Embodiment 1. As illustrated in FIG. 1, the multistatic array radar 20 includes a sensor 30 and an image reconstructor 40.

The sensor 30 includes a transmitter 31, a receiver 32, a case 33, and a curvilinear array antenna 37. The curvilinear array antenna 37 includes a plurality of antenna elements 36 which are aligned. The plurality of antenna elements 36 each includes a transmitting antenna element 36a and a receiving antenna element 36b.

The transmitting antenna element 36a transmits waves toward an object, specifically, a living body, and the receiving antenna element 36b receives reflected waves (scattered waves) that are waves reflected off (scattered by) the living body. Microwaves are cited herein as an example of the waves, but the waves are not limited to microwaves and may be electromagnetic waves or ultrasonic waves in other bands. Accordingly, the transmitting antenna element 36a and the receiving antenna element 36b may be antenna elements for microwaves or may be antenna elements not only for microwaves but also for electromagnetic waves or ultrasonic waves in other bands. Wideband or ultrawideband antenna elements may also be used to keep pace with a recent increase in bandwidth in the mobile telecommunication technology. Ultrawideband antennas will be described later in detail.

The transmitter 31 adjusts (i) the timing of transmitting microwaves that are to be radiated from the transmitting antenna element 36a, (ii) the number of times the microwaves are transmitted, and (iii) the transmission gain of the microwaves.

The receiver 32 conveys to the image reconstructor 40 data of scattered waves of the microwaves received by the receiving antenna element 36b. At this time, the received data of scattered waves may be amplified or be subjected to signal processing, such as A/D conversion, by the receiver 32.

The case 33 has a conical shape. A subject to be observed (an examination subject), for example, a breast, is placed in the case 33. The diameter of the circular base is 10 cm, for example. The curvilinear array antenna 37 is aligned on the case 33, along the generatrix from the vertex to the base of the case 33. In other words, the transmitting antenna elements and the receiving antenna elements are aligned in the same direction as the axis of rotational symmetry of the case 33, at least when seen in a plan view from one direction. The axis of rotational symmetry of the case 33 indicates a straight line connecting the vertex of the cone to the center of the base of the cone.

The image reconstructor 40 analyzes the data of scattered waves conveyed from the receiver 32 and visualizes the data of scattered waves using a later-described image reconstruction algorithm. Thus, images corresponding to information on the interior of an object are reproduced on an image display 50.

When the above-described curvilinear array antenna 37 in the multistatic array radar 20 moves in the circumferential direction of the base of the cone, $n_x n_y^2$ sets of time-series data items are obtained. With $n_t$ time series, the number of data items to be obtained is $n_x n_y^2 n_t$ in total. The information quantity of the $n_x n_y^2 n_t$ data items obtained in this way has $n_y$ times greater redundancy than $n_x n_y n_t$ data items necessary for three-dimensional visualization. Therefore, adapting this data to a visualization function in the later-described image reconstruction algorithm allows three-dimensional images according to information on the interior of an object to be reproduced with higher precision.

Furthermore, the distance between the transmitting antenna element 36a and the receiving antenna element 36b can be freely chosen, meaning that the gain of waves can be changed according to a pair of the transmitting antenna element 36a and the receiving antenna element 36b (a path-dependent variable gain amplification function) to change the depth of an object to which the inspection is possible. The arrangement of the transmitting antenna element 36a and the receiving antenna element 36b will be described later in detail.

The following describes a process flow of visualizing information on the interior of a living body, specifically, information on the position of a cancer cell in a breast, according to the scattering tomography method.

Process Flow of Scattering Tomography Method

Figure 2:
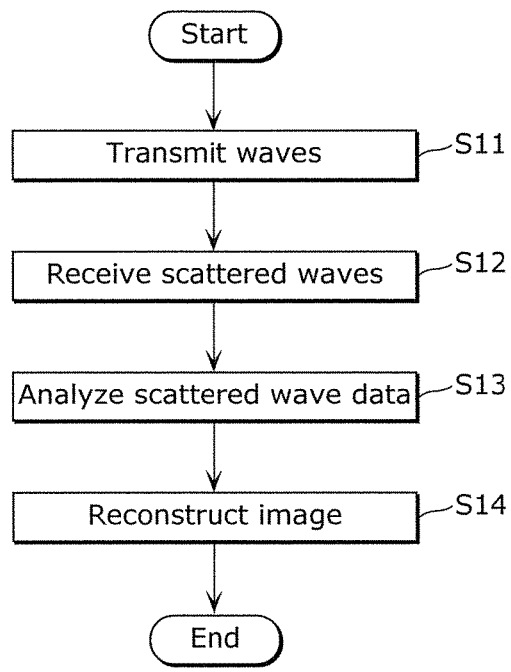
FIG. 2 is a flowchart representing operations of a multistatic array radar according to Embodiment 1.

FIG. 2 is a flowchart representing operations of the multistatic array radar 20 illustrated in FIG. 1.

As illustrated in FIG. 2, a method of visualizing (imaging) information on the interior of a living body according to the scattering tomography method is as follows.

First, waves are radiated from the transmitting antenna elements 36a toward an object placed in the case 33, specifically, a breast (S11). As the waves, microwaves are used, for example. The transmitter 31 adjusts the wavelength, the amplitude, and the like of microwaves, and the transmitting antenna elements 36a radiate the adjusted ultrasonic waves to the breast.

Next, reflected waves (scattered waves) that have been reflected off normal cells and cancer cells in the breast are received by the receiving antenna elements 36b (S12). Normal cells and cancer cells have different permittivities, resulting in the scattered waves having different intensities. The received scattered waves may be, for example, amplified or subject to A/D conversion by the receiver 32, that is, may be converted into a type suitable for analysis that is performed by the image reconstructor 40.

Next, scattered wave data representing the received scattered waves are conveyed from the receiver 32 to the image reconstructor 40. The image reconstructor 40 analyzes the conveyed scattered wave data (S13). Herein, the scattered wave data is analyzed using the later-described image reconstruction algorithm. Specifically, a visualization function is derived. With this, images (an image) corresponding to normal cells and cancer cells in the breast are reconstructed (S14).

Furthermore, data of the reconstructed images is conveyed from the image reconstructor 40 to the image display 50 and reproduced on the image display 50. This makes it possible to check the presence of a cancer cell in the breast and the position, shape, and size of the cancer cell.

Hereinafter, the image reconstruction algorithm that is used by the image reconstructor 40 is described. This image reconstruction algorithm is a principle of the scattering tomography method for a conical model having a linear generatrix according to this embodiment.

Image Reconstruction Algorithm

Figure 3:
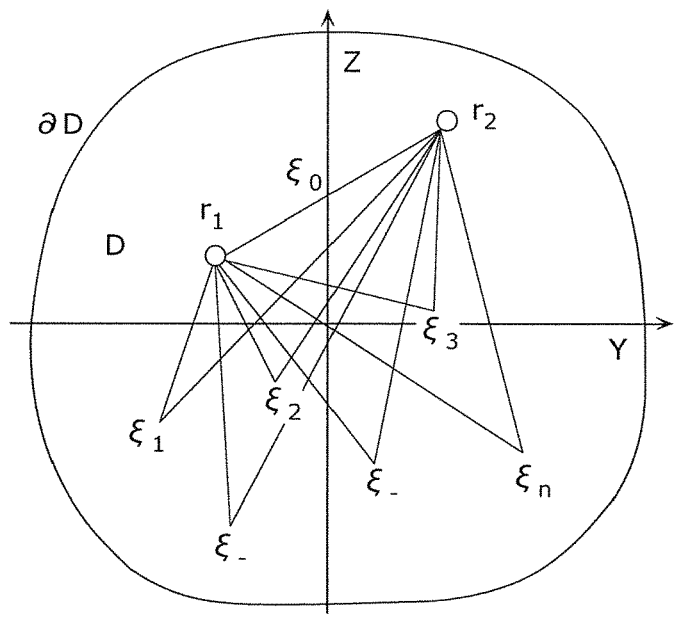
FIG. 3 illustrates an analysis model for explaining a principle of a scattering tomography method according to Embodiment 1.
Figure 4:
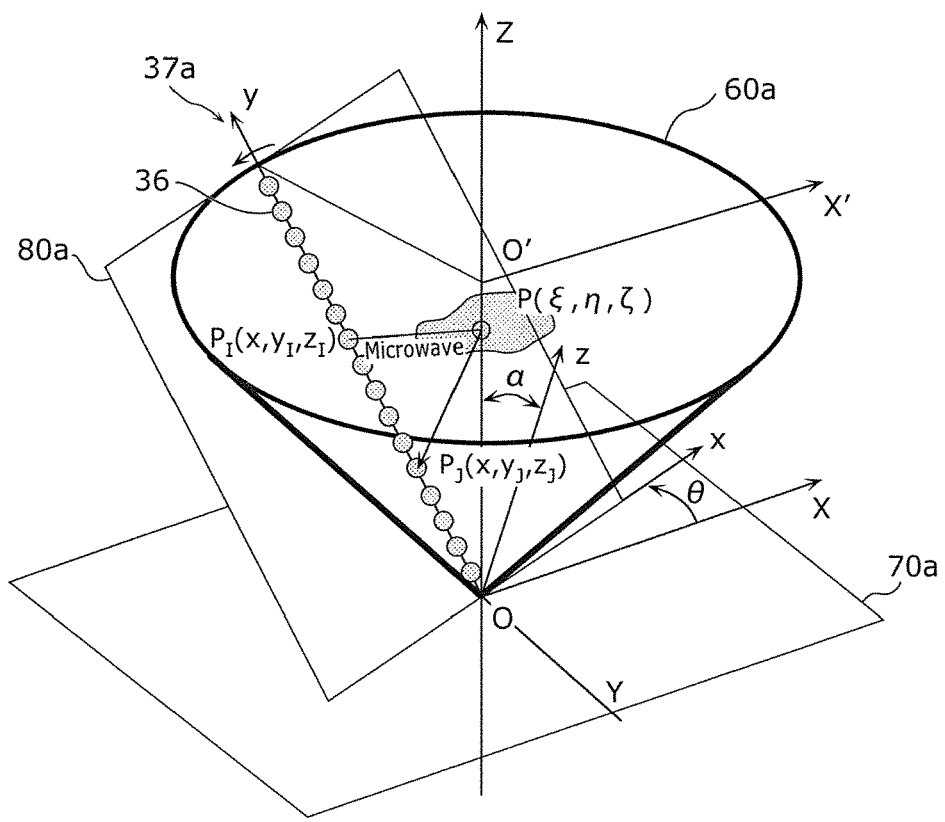
FIG. 4 illustrates an analysis model for explaining a principle of a scattering tomography method according to Embodiment 1.
Figure 5:
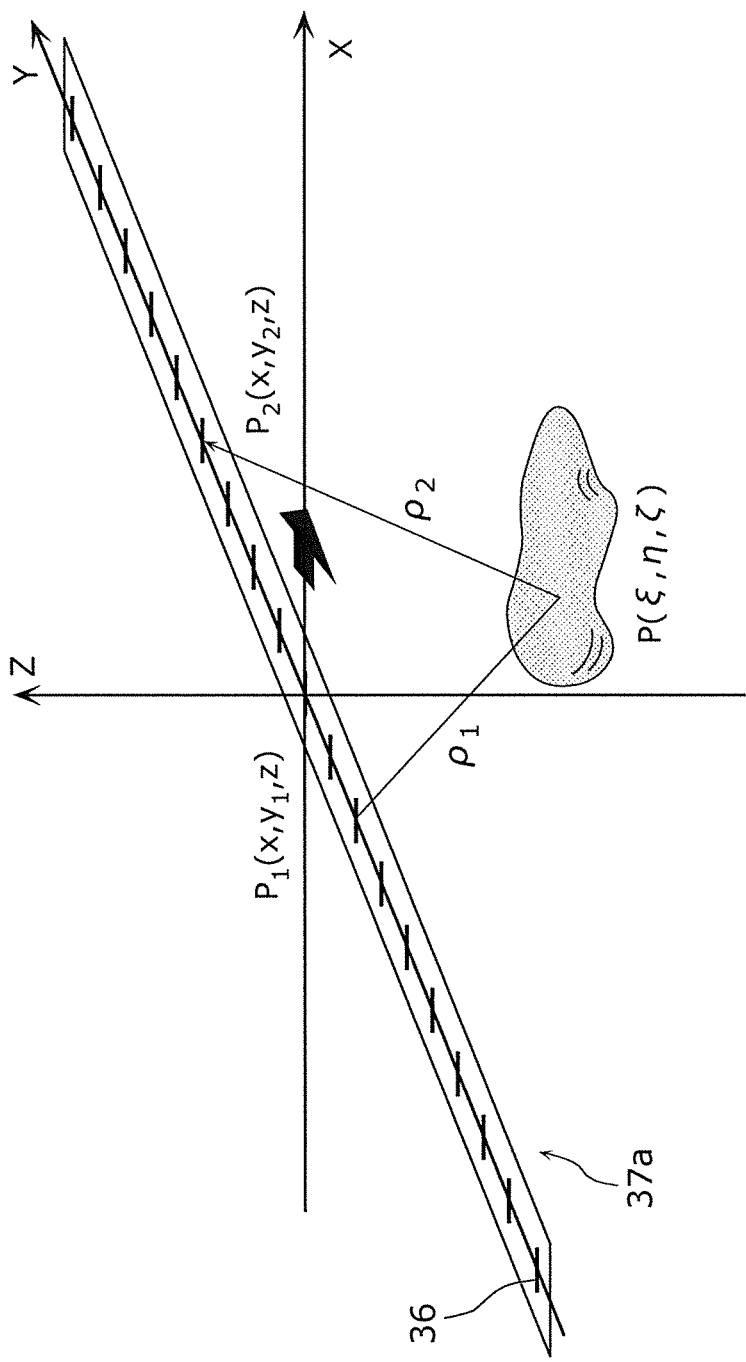
FIG. 5 illustrates an analysis model for explaining a principle of a scattering tomography method according to Embodiment 1.

FIG. 3 to FIG. 5 illustrate an analysis model for explaining a principle of a scattering tomography method according to this embodiment. The following describes derivation of a visualization function that is applied in the case where the sensor 30 is a one-dimensional sensor array, using the model illustrated in FIG. 3 to FIG. 5 as an analysis model.

In the case of the image reconstruction algorithm (theory) described below, it is assumed that the subject to be visualized is a conical body having a linear generatrix. This conical body is used as an analysis model, and a wave radiation point (the transmitting antenna element 36a) and a wave receiving point (the receiving antenna element 36b) are arbitrarily arranged on the generatrix. Information on the interior of an object is then visualized using transmitted data representing waves radiated from the wave radiation point and scattered wave data representing scattered waves received at the wave receiving point.

A brief mathematical explanation of the image reconstruction algorithm is as follows: a scattering field function necessary for visualization is set first, a scattering field equation is constructed from the function, and an exact solution is determined using transmitted data and received data, that is, the inverse problem is solved.

More specifically, the Green's function (a reconstruction function) for visualization is set first. A partial differential equation (a scattering field equation) in a five-dimensional space (t, x, $y_1$, $y_2$, z), the solution of which is this Green's function, is then constructed. This partial differential equation is then solved using, as a boundary condition, the transmitted data of waves radiated from the transmitting antenna elements 36a arranged in a curve and the received data of waves received by the receiving antenna elements 36b arranged in the curve, and an exact solution is determined where t→0, x→x, $y_1$→$y_2$ (=y), and z→z. Thus, the visualization function including an exact solution (function) is determined, allowing information on the interior of an object to be visualized at high speed and with high precision in a versatile manner.

A specific example is as follows.

1. Inverse Problem of Scattering and the Green's Function

Suppose a situation where waves radiated from $r_1$ are reflected at a point $\xi$ and travel to a point $r_2$ as in FIG. 3. Under the condition that a frequency $\omega$ is constant, the wave transmitting point $r_1$ and the wave receiving point $r_2$ freely move inside an x cross-section D (a side surface of a conical body 60a) while the wave transmitting point $r_1$ and the wave receiving point $r_2$ satisfy a certain constraint. Data obtained in this case is denoted by $G(r_1, r_2, \omega)$. This function relates to distribution of reflection points within a region. Herein, $\omega=2\pi f$ where $\omega$ represents an angular frequency. $G(r_1, r_2, \omega)$ is a sum of reflected signals from all the points $\xi$. Since there are many reflection points within the region, $G(r_1, r_2, \omega)$ can be written as in Expression 1.

[Math. 1]

$$G(r_1, r_2, \omega) = \iiint_D \varphi(r_1 \to \xi \to r_2, \omega) d\xi \quad \text{Expression 1}$$

In this equation, [Math. 2] represents signal intensity of the waves radiated from the point $r_1$, reflected at the point $\xi$, and traveled to the point $r_2$.

[Math. 2]

$$\varphi(r_1 \to \xi \to r_2, \omega)$$

The constraint that restricts the wave transmitting point $r_1$ and the wave receiving point $r_2$ is a condition that the x-coordinate of $r_1$ and the x-coordinate of $r_2$ are always equal.

A theoretical structure of the inverse problem of scattering is described using this function $G(r_1, r_2, \omega)$.

A partial region of a three-dimensional space is denoted by D, and a boundary of the region is denoted by ∂D. In this case, the function $G(r_1, r_2, \omega)$ is a solution of a differential equation such as Expression 2 below inside the region D.

$$L\left(\frac{\partial}{\partial t}, \frac{\partial}{\partial r_1}, \frac{\partial}{\partial r_2}\right) \overline{G}(r_1, r_2, t) = 0 \quad \text{[Math. 3]}$$

where $\overline{G}(r_1, r_2, t)$ is a function obtained by the Fourier transform of $G(r_1, r_2, \omega)$ with respect to $\omega$ . . . . Expression 2

The value of $G(r_1, r_2, \omega)$ at the boundary ∂D is a value measured by the sensor 30 (the transmitted data and the received data). The above equation is solved under this boundary condition, and based on the result, $\rho(r)$ is defined as Expression 3 below.

[Math. 4]

$$\rho(r) = \lim_{t \to 0} [Tr[\overline{G}(r_1, r_2, t)]] = \overline{G}(r, r, 0) \quad \text{Expression 3}$$

Herein, $\rho(r)$ is a function related to a slope of permittivity within the region D that is to be determined. In practice, it is necessary to determine a differential operator $L(\partial/\partial t, \partial/\partial r_1, \partial/\partial r_2)$ expressed above.

2. Theory of Multistatic Inverse Scattering on Curved Surface of Rotational Symmetry Using Conical Analysis Model Next, a method of determining the above-mentioned differential operator is described. FIG. 4 and FIG. 5 illustrate an analysis model for describing the method of determining a differential operator.

In the analysis model according to this embodiment, it is assumed that the subject to be visualized is the conical body 60a having a linear generatrix as illustrated in FIG. 4. A plurality of antenna elements 36 are aligned along the generatrix of the conical body 60a. The plurality of antenna elements 36 constitute a curvilinear array antenna 37a. In the curvilinear array antenna 37a illustrated in FIG. 4, the curvilinear array antenna 37a rotates about the axis passing through the vertex of the conical body 60a and the center of the base of the conical body 60a. In other words, the transmitting antenna elements 36a and the receiving antenna elements 36b are aligned in the same direction with the axis of rotational symmetry of the case 33, at least when seen in a plan view from one direction. The axis of rotational symmetry of the case 33 indicates a straight line connecting the vertex of the cone to the center of the base of the cone.

More specifically, suppose a tangent plane 80a of the conical body 60a at the position of the curvilinear array antenna 37a, and it is assumed that this virtual tangent plane 80a rotates, and scattered wave data can be obtained for every angle θ of the rotation. A three-dimensional structure of the interior of the conical body 60a is reconstructed from such multistatic times-series data in a surface of the conical body 60a. This theory is described below.

In this analysis model, suppose that the vertex of the conical body 60a is point O, and the center of the circular base of the conical body 60a is point O' as illustrated in FIG. 4. The direction from the point O to the point O' is the Z direction (Z-axis direction). The plane passing through the point O and parallel to the base of the conical body 60a is referred to as a reference plane 70a. An arbitrary one direction in the reference plane 70a is the X direction (X-axis direction), and the direction perpendicular to the X direction in the reference plane 70a is the Y direction (Y-axis direction).

In the base of the conical body 60a, the direction parallel to the X direction is referred to as an X' direction (X'-axis direction), and the direction parallel to the Y direction is referred to as a Y' direction (Y'-axis direction).

On the side surface of the conical body 60a, the plane contacting the conical body 60a at the position of the curvilinear array antenna 37a is the tangent plane 80a. One direction of the cross line on which this tangent plane 80a and the reference plane 70a interest with each other is the x direction (x-axis direction). On the tangent plane 80a, the direction from the point O toward the base of the conical body 60a is the y direction (y-axis direction). The direction perpendicular to the x direction and the y direction is the z direction (z-axis direction).

On the reference plane 70a, the x axis rotates about the Z axis, and the angle between the X axis and the x axis is denoted by θ. The angle between the Z axis and the z axis is denoted by α.

FIG. 5 is a partially enlarged schematic view of the curvilinear array antenna 37a illustrated in FIG. 4.

Multistatic coordinates $y_1$ and $y_2$ are defined on the y axis in FIG. 5, and the following reconstruction theory was established. Note that regarding the x-coordinate, data of one point (x=0, $y_1$, $y_2$) is obtained on the tangent plane 80a in the following theory.

As illustrated in FIG. 5, waves radiated from the transmitting antenna element 36a at point $P_1(x, y_1, z)$ in the curvilinear array antenna 37a are received by the receiving antenna element 36b at point $P_2(x, y_2, z)$ in the curvilinear array antenna 37a. In addition, assume that the measurement point $P_2$ moves on an arbitrary straight line in which the curvilinear array antenna 37 is located.

The y-z coordinates of $r_1$ and $r_2$ on an arbitrary straight line are expressed as $r_1=(x, y_1, z_1)$ and $r_2=(x, y_2, z_2)$. In this case, the function G is defined as Expression 4 below.

[Math. 5]

$$G(r_1, r_2, \omega) = \iiint_D \varphi(r_1 \to \xi \to r_2, \omega) d\xi \qquad \text{Expression 4}$$

Next, a function φ such as Expression 5 below is introduced as an equation which the function $G(r_1, r_2, \omega)$ satisfies. This means that when the point P moves throughout the region, a signal received at P2 is represented as the following Expression 5. In this case, the following relationships hold: $\omega=ck$ and $k=2\pi/\lambda$ where c is a speed of propagation; k is a wave number; and λ is a wavelength. In Expression 5: φ corresponds to a reconstruction function (a solution) for reconstructing an image relating to information on the interior of an object according to the present invention; and ξ, η, and ζ are the x-coordinate, the y-coordinate, and the z-coordinate, respectively, of the point P (ξ, η, ζ) illustrated in FIG. 4 and FIG. 5. The point P (ξ, η, ζ) is an arbitrary scattering point within the region.

[Math. 6]

$$\varphi(x, y_1, y_2, z) = \iint\int_D \frac{e^{ik\rho_1}}{\rho_1} \frac{e^{ik\rho_2}}{\rho_2} \varepsilon(\xi, \eta, \zeta) d\xi d\eta d\zeta \qquad \text{Expression 5}$$

$$\rho_1 = \sqrt{(x-\xi)^2 + (y_1-\eta)^2 + (z-\zeta)^2}$$

$$\rho_2 = \sqrt{(x-\xi)^2 + (y_2-\eta)^2 + (z-\zeta)^2}$$

Herein, it is assumed that a time factor is proportional to exp(−iωt). The kernel function in the term to be integrated in the above expression is denoted by Φ.

[Math. 7]

$$\phi = \frac{e^{ik\rho_1}}{\rho_1} \frac{e^{ik\rho_2}}{\rho_2}$$

A partial differential equation, the scattering field function of which is this expression or a value obtained by differentiating and integration this expression with respect to ξ, η, ζ or the like is determined. In order for this to be done, high-order terms may be ignored in calculation for 1/ρ resulting from the differentiation.

Here, an abridged notation for differentiation is defined as Expression 6 below.

[Math. 8]

$$\frac{\partial}{\partial t} \to \partial_t, \; \frac{\partial}{\partial x} \to \partial_x, \; \frac{\partial}{\partial y_1} \to \partial_{y_1}, \; \frac{\partial}{\partial y_2} \to \partial_{y_2}, \; \frac{\partial}{\partial z} \to \partial_z \qquad \text{Expression 6}$$

The orders of Φ are differentiated using Expression 6. Expression 7 below is obtained.

[Math. 9]

$$\partial_x \phi = ik(x-\xi)\left(\frac{1}{\rho_1}+\frac{1}{\rho_2}\right)\phi + o(\rho^{-3})$$

$$\partial_{y_1}\phi = ik\frac{y_1-\eta}{\rho_1}\phi + o(\rho^{-3})$$

$$\partial_{y_2}\phi = ik\frac{y_2-\eta}{\rho_2}\phi + o(\rho^{-3})$$

$$\partial_z \phi = ik(z-\zeta)\left(\frac{1}{\rho_1}+\frac{1}{\rho_2}\right)\phi + o(\rho^{-3})$$

$$\partial_x \partial_x \phi = (ik)^2 (x-\xi)^2 \left(\frac{1}{\rho_1}+\frac{1}{\rho_2}\right)^2 \phi + o(\rho^{-3})$$

$$\partial_z \partial_z \phi = (ik)^2 (z-\zeta)^2 \left(\frac{1}{\rho^1}+\frac{1}{\rho_2}\right)^2 \phi + o(\rho^{-3})$$

$$\partial_{y_1}\partial_{y_1}\phi = (ik)^2 \left(\frac{y_1-\eta}{\rho_1}\right)^2 \phi + o(\rho^{-3})$$

$$\partial_{y_2}\partial_{y_2}\phi = (ik)^2 \left(\frac{y_2-\eta}{\rho_2}\right)^2 \phi + o(\rho^{-3})$$

Expression 7

In the expressions below, the terms o(*), which are complicated, are omitted. Note that * means an arbitrary variable. The sum of four expressions involving the second order differential is as in Expression 8 below.

[Math. 10]

$$\Delta_4 \phi = \left(\partial_x^2 + \partial_{y_1}^2 + \partial_{y_2}^2 + \partial_z^2\right)\phi$$

$$= (ik)^2 \left\{2 + 2\frac{(x-\xi)^2 + (z-\zeta)^2}{\rho_1 \rho_2}\right\}\phi$$

Expression 8

The both sides of Expression 8 are reorganized into Expression 9.

[Math. 11]

$$\{\Delta_4 - 2(ik)^2\}\phi = 2(ik)^2 \frac{\rho_1^2 - (y_1-\eta)^2}{\rho_1 \rho_2}\phi$$

$$= 2(ik)^2 \frac{\rho_2^2 - (y_2\eta)^2}{\rho_1 \rho_2}\phi$$

Expression 9

Operating the operator in the left side of Expression 9 twice leads to Expression 10 below.

[Math. 12]

$$\{\Delta_4 - 2(ik)^2\}^2 \phi = 4(ik)^2 \frac{\{\rho_1^2-(y_1-\eta)^2\}\{\rho_2^2-(y_2-\eta)^2\}}{\rho_1^2 \rho_2^2}\phi$$

$$= 4(ik)^4 \{1-(ik)^{-2}\partial_{y_1}^2\}\{1-(ik)^{-2}\partial_{y_2}^2\}\phi$$

Expression 10

This is reorganized into Expression 11 below.
[Math. 13]

$$[\tfrac{1}{4}\{\Delta_4 - 2(ik)^2\}^2 - \partial_{y_1}^2 \partial_{y_2}^2 + (ik)^2(\partial_{y_1}^2 + \partial_{y_2}^2) - (ik)^4]\phi = 0 \quad \text{Expression 11}$$

Although a steady-state case is assumed in derivation of Expression 11, it is easy to extend Expression 11 to an unsteady-state case. In order to extend Expression 11 to an unsteady-state case, a variable in Expression 11 is replaced as in Expression 12 below.

[Math. 14]

$$-ik \rightarrow \frac{1}{c}\partial_t \quad \text{Expression 12}$$

This leads to the equation in Expression 13 below in the end. Note that Expression 13 corresponds to a scattering field equation according to the present invention.

[Math. 15]

$$\left\{\Delta_4^2 - \frac{4}{c^2}(\partial_t^2 \partial_x^2 + \partial_t^2 \partial_z^2) - 4\partial_{y_1}^2 \partial_{y_2}^2\right\}\phi = 0 \quad \text{Expression 13}$$

$$\Delta_4 = \partial_x^2 + \partial_{y_1}^2 + \partial_{y_2}^2 + \partial_z^2$$

In Expression 13, the differential is applied to an integral kernel, resulting in φ also satisfying the above partial differential equation. This equation is a four-dimensional pseudo wave equation involving five variables t, x, $y_1$, $y_2$, and z.

Expression 13 is solved using the Fourier transform. First, the multi-dimensional Fourier transform of φ with respect to t, x, $y_1$, and $y_2$ results in Expression 14 below.

[Math. 16]

$$\tilde{\varphi}(k_x, k_{y_1}, k_{y_2}, z, \omega) = \int_{-\infty}^{\infty} e^{i\omega t} dt \int_{-\infty}^{\infty} e^{ik_{y_1}y_1} dy_1$$

$$\int_{-\infty}^{\infty} e^{ik_{y_2}y_2} dy_2 \int_{-\infty}^{\infty} e^{ik_x x}\varphi(x, y_1, y_2, z, t) dx$$

Expression 14

Expression 15 below is obtained by writing the differentials with respect to z in Expression 14 as $D_z$.
[Math. 17]

$$\{(D_z^2 - k_x^2 - k_{y_1}^2 - k_{y_2}^2)^2 + 4k^2(D_z^2 - k_x^2) - 4k_{y_1}^2 k_{y_2}^2\}\tilde{\varphi} = 0 \quad \text{Expression 15}$$

Here, with the use of the relation ω=ck, four elementary solutions of this equation in Expression 15 are as follows.

[Math. 18]

$$E_1 = e^{i\left\{\sqrt{\left(\sqrt{k^2-k_{y_1}^2}+\sqrt{k^2-k_{y_2}^2}\right)^2 - k_x^2}\right\}z}$$

$$E_2 = e^{-i\left\{\sqrt{\left(\sqrt{k^2-k_{y_1}^2}+\sqrt{k^2-k_{y_2}^2}\right)^2 - k_x^2}\right\}z}$$

$$E_3 = e^{i\left\{\sqrt{\left(\sqrt{k^2-k_{y_1}^2}+\sqrt{k^2-k_{y_2}^2}\right)^2 - k_x^2}\right\}z}$$

$$E_4 = e^{-i\left\{\sqrt{\left(\sqrt{k^2-k_{y_1}^2}+\sqrt{k^2-k_{y_2}^2}\right)^2 - k_x^2}\right\}z}$$

Expression 16

In Expression 16, $E_1$ is the only meaningful solution in light of the situation that the time factor is $e^{-i\omega t}$, a phase is added depending on the path of radiated radio waves, and radio waves reflected in an object return toward the measurement surface. Therefore, Expression 17 below is obtained.

[Math. 19]

$$\tilde{\varphi}(k_x, k_{y_1}, k_{y_2}, z, k) = a(k_x, k_{y_1}, k_{y_2}, k) e^{i\left\{\sqrt{\left(\sqrt{k^2-k_{y_1}^2}+\sqrt{k^2-k_{y_2}^2}\right)^2 - k_x^2}\right\} z}$$

Expression 17

The Fourier transform of this expression leads to the following solution $\varphi$ for the wave equation in Expression 13.

[Math. 20]

$$\phi(x, y_1, y_2, z, k) =$$

Expression 18

$$\frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a(k_x, k_{y_1}, k_{y_2}, k)$$

$$e^{i\left\{\sqrt{\left(\sqrt{k^2-k_{y_1}^2}+\sqrt{k^2-k_{y_2}^2}\right)^2 - k_x^2}\right\} z} dk_x dk_{y_1} dk_{y_2}$$

Since the measured data includes only the case of x=0, Expression 19 below holds.
[Math. 21]

$$\phi(x, y_1, y_2, 0, k) = \varphi_R(y_1, y_2, k)\delta(x)$$

Expression 19

Applying this expression to the above expression where z=0 leads to Expression 20 below.

[Math. 22]

$$\phi_R(y_1, y_2, k)\delta(x) =$$

Expression 20

$$\frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a(k_x, k_{y_1}, k_{y_2}, k) dk_x dk_{y_1} dk_{y_2}$$

The Fourier transform of the both sides of Expression 20 with respect to (x, $y_1$, $y_2$) results in a ($k_x$, $k_{y1}$, $k_{y2}$, k) being determined as follows.

[Math. 23]

$$a(k_x, k_{y_1}, k_{y_2}, k) = \tilde{\phi}_R(k_{y_1}, k_{y_2}, k)$$

Expression 21

In this way, the solution $\varphi(x, y_1, y_2, z, k)$ of the partial differential equation is obtained.

The traces of $y_1$ and $y_2$ of the function $\varphi(x, y_1, y_2, z, k)$ are taken. Specifically, first, in the visualization function, suppose $y_1 \to y$ and $y_2 \to y$ on the condition that k and z are fixed.

[Math. 24]

$$\phi(x, y, y, z, k) = \lim_{y_1 \to y}[\phi(x, y_1, y, z, k)]$$

Expression 22

$$= \lim_{y_1 \to y}\left[\frac{1}{(2\pi)^3}\int_{-\infty}^{\infty}\int_{-\infty}^{\infty}\int_{-\infty}^{\infty} e^{-i(k_x x + k_{y_1} y_1 + k_{y_2} y)} a(k_x, k_{y_1}, k_{y_2}, k) e^{iz\left\{\sqrt{\left(\sqrt{k^2-k_{y_1}^2}+\sqrt{k^2-k_{y_2}^2}\right)^2 - k_x^2}\right\}} dk_x dk_{y_1} dk_{y_2}\right]$$

$$= \lim_{y_1 \to y}\left[\frac{1}{(2\pi)^3}\int_{-\infty}^{\infty}\int_{-\infty}^{\infty}\int_{-\infty}^{\infty} e^{-i(k_x x + k_{y_1} y_1 + k_{y_2} y)} \tilde{\phi}_R(k_{y_1}, k_{y_2}, k) e^{iz\left\{\sqrt{\left(\sqrt{k^2-k_{y_1}^2}+\sqrt{k^2-k_{y_2}^2}\right)^2 - k_x^2}\right\}} dk_x dk_{y_1} dk_{y_2}\right]$$

$$= \lim_{y_1 \to y}\left[\frac{1}{(2\pi)^3}\int_{-\infty}^{\infty}\int_{-\infty}^{\infty}\int_{-\infty}^{\infty} e^{-i(k_x x + k_{y_1} y_1 + k_{y_2} y)} e^{ik_z z} \tilde{\phi}_R(k_{y_1}, k_{y_2}, k) dk_x dk_{y_1} dk_{y_2}\right]$$

In order to perform the integration with respect to k, the variables are transformed as in Expression 23 below.

[Math. 25]

$$k_z = \sqrt{\left(\sqrt{k^2-k_{y_1}^2}+\sqrt{k^2-k_{y_2}^2}\right)^2 - k_x^2}$$

Expression 23

$$k = \frac{1}{2}\sqrt{k_x^2 + k_z^2 + \frac{(k_{y_1}^2 - k_{y_2}^2)^2}{k_x^2 + k_z^2} + 2(k_{y_1}^2 + k_{y_2}^2)}$$

$$\frac{dk}{dk_z} = \frac{k_z\sqrt{k^2-k_{y_1}^2}\sqrt{k^2-k_{y_2}^2}}{k(k_x^2 + k_z^2)}$$

Next, Expression 22 is Fourier transformed with respect to k, and t=0 is applied thereto. Then, the visualization function $\rho(r, \theta)$ in the local coordinate system at the angle $\theta$ is determined as indicated in Expression 24.

Here, Math. 26 is dependent on $\theta$ and therefore is written as in Math. 27 in order to explicitly show the $\theta$ dependency.

[Math. 26]

$$\tilde{\phi}_R(k_{y_1}, k_{y_2}, k)$$

[Math. 27]

$$\tilde{\phi}_R(k_{y_1}, k_{y_2}, k, \theta)$$

[Math. 28]

$$\rho(x, y, z, \theta) = \int_{-\infty}^{\infty} \phi(x, y, y, z, k) dk$$

$$= \int_{-\infty}^{\infty} \lim_{y_1 \to y} [\phi(x, y_1, y, z, k)] dk$$

$$= \int_{-\infty}^{\infty} \lim_{y_1 \to y} \left[ \frac{1}{(2\pi)^3} \int_{-\infty}^{\infty} \int_{-\infty}^{\infty} \int_{-\infty}^{\infty} e^{-i(k_x x + k_{y1} y_1 + k_{y2} y)} a(k_x, k_{y_1}, k_{y_2}, k) e^{i\left\{\sqrt{\left(\sqrt{k^2-k_{y_1}^2}+\sqrt{k^2-k_{y_2}^2}\right)^2-k_x^2}\right\}z} dk_x dk_{y_1} dk_{y_2} \right] dk$$

$$= \int_{-\infty}^{\infty} \lim_{y_1 \to y} \left[ \frac{1}{(2\pi)^3} \int_{-\infty}^{\infty} \int_{-\infty}^{\infty} \int_{-\infty}^{\infty} e^{-i(k_x x + k_{y1} y_1 + k_{y2} y)} e^{ik_z z} \tilde{\phi}_R(k_{y_1}, k_{y_2}, k, \theta) \left(\frac{dk}{dk_z}\right) dk_x dk_{y_1} dk_{y_2} dk_z \right]$$

Expression 24

Furthermore, the results obtained at angles θ are integrated, leading to the three-dimensional reconstructed image represented by Expression 25.

[Math. 29]

$$P(X, Y, Z) = \int_0^{2\pi} \rho(x, y, z, \theta) d\theta$$

Expression 25

Next, the result of calculation in the tangent space is transformed into data in the global coordinate system (X, Y, Z). Assuming that the projection of the y-axis onto the (X, Y) plane is y', Expression 26 below holds.

[Math. 30]

$$y = y' \cos \alpha + Z \sin \alpha$$

$$z = -y' \sin \alpha + Z \cos \alpha$$

Expression 26

Expression 27 below represents further transformation from (x, y') to (X, Y).

[Math. 31]

$$x = X \cos \theta + Y \sin \theta$$

$$y' = -X \sin \theta + Y \cos \theta$$

Expression 27

Expression 28 below is given about x, y, and z by summarizing the foregoing.

[Math. 32]

$$x = X \cos \theta + Y \sin \theta$$

$$y = -X \cos \alpha \sin \theta + Y \cos \alpha \cos \theta + Z \sin \alpha$$

$$z = X \sin \alpha \sin \theta - Y \sin \alpha \cos \theta + Z \cos \alpha$$

Expression 28

These transformation formulae are applied to Expression 29 below.

[Math. 33]

$$\rho(x, y, z, \theta) = \frac{1}{(2\pi)^3} \int_{-\infty}^{\infty} \int_{-\infty}^{\infty} \int_{-\infty}^{\infty} \int_{-\infty}^{\infty} e^{-i(k_x x + k_{y1} y + k_{y2} y)} e^{ik_z z} \tilde{\phi}_R(k_{y_1}, k_{y_2}, k, \theta) \left(\frac{dk}{dk_z}\right) dk_x dk_{y_1} dk_{y_2} dk_z$$

Expression 29

Furthermore, the variables in Expression 30 below are introduced.

[Math. 34]

$$k_{ye} = k_{y_1} + k_{y_2}$$

$$k_{yo} = k_{y_1} - k_{y_2}$$

Expression 30

Through the introduction of Expression 30, Expression 29 results in Expression 31 below.

[Math. 35]

$$\rho(x, y, z, \theta) = \frac{1}{2(2\pi)^3} \lim_{y_o \to 0} \int_{-\infty}^{\infty} \int_{-\infty}^{\infty} \int_{-\infty}^{\infty} \int_{-\infty}^{\infty} e^{-i(k_x x + k_{ye} y + k_{yo} y_o - k_z z)} \tilde{\phi}_R(k_{y_1}, k_{y_2}, k, \theta) \left(\frac{dk}{dk_z}\right) dk_x dk_{ye} dk_{yo} dk_z$$

Expression 31

Furthermore, the variable transformation in Expression 32 below is performed in a region of the spectrum.

Note that the variables ξ, η, and ζ in Expression 32 and Expression 33 below are different from the coordinates of point P (ξ, η, ζ) in FIG. 5, Expression 5, etc.; they are new variables used for the variable transformation.

[Math. 36]

$$\xi = -k_x \cos\theta + (k_{ye}\cos\alpha + k_z\sin\alpha)\sin\theta$$

$$\eta = -k_x \sin\theta - (k_{ye}\cos\alpha + k_z\sin\alpha)\cos\theta$$

$$\zeta = -k_{ye}\sin\alpha + k_z\cos\alpha \qquad \text{Expression 32}$$

The inverse transformation for Expression 32 is given by Expression 33.

[Math. 37]

$$k_x = -\xi\cos\theta - \eta\sin\theta$$

$$k_{ye} = (\xi\sin\theta - \eta\cos\theta)\cos\alpha - \zeta\sin\alpha$$

$$k_z = (\xi\sin\theta - \eta\cos\theta)\sin\alpha + \zeta\cos\alpha \qquad \text{Expression 33}$$

The reconstruction function at the angle θ is represented as in Expression 34 below.

[Math. 38]

Expression 34

$$\rho(x,y,z,\theta) = \frac{1}{2(2\pi)^3}\lim_{y_o\to 0}\int_{-\infty}^{\infty}\int_{-\infty}^{\infty}\int_{-\infty}^{\infty}\int_{-\infty}^{\infty} e^{i(\xi X + \eta Y + k_{yo}y_o + \zeta Z)}\tilde{\phi}_R(k_{y_1},k_{y_2},k,\theta)\left(\frac{dk}{dk_z}\right)dk_x dk_{y_e} dk_{y_o} dk_z$$

$$= \frac{1}{2(2\pi)^3}\lim_{y_o\to 0}\int_{-\infty}^{\infty}\int_{-\infty}^{\infty}\int_{-\infty}^{\infty}\int_{-\infty}^{\infty} e^{-i(\xi X + \eta Y + k_{yo}y_o + \zeta Z)}\tilde{\phi}_R(k_{y_1},k_{y_2},k,\theta)\left(\frac{dk}{dk_z}\right)d\xi d\eta dk_{y_o} d\zeta$$

$$\frac{dk}{dk_z} = \frac{k_z\sqrt{k^2 - k_{y_1}^2}\sqrt{k^2 - k_{y_2}^2}}{k(k_x^2 + k_z^2)}$$

$$k = \frac{1}{2}\sqrt{k_x^2 + k_z^2 + \frac{(k_{y_1}^2 - k_{y_2}^2)^2}{k_x^2 + k_z^2} + 2(k_{y_1}^2 + k_{y_2}^2)}$$

Here, since $k_x$, $k_{y1}$, $k_{y2}$, and $k_z$ are functions of $\xi$, $\eta$, $\zeta$, and $k_{yo}$ as in Expression 30 and Expression 33, it is possible to transform the data in the local coordinates at the angle θ into data in the global coordinates by using the Fourier transform only.

In the end, the data is integrated with respect to the angle θ, resulting in the reconstruction image, that is, the visualization function as in Expression 35.

[Math. 39]

$$P(X,Y,Z) = \int_0^{2\pi} \rho(x,y,z,\theta)d\theta \qquad \text{Expression 35}$$

With this visualization function, an image relating to information on the interior of an object can be reconstructed.

Reconstructed Image obtained by Scattering Tomography Method

Effects produced by obtaining a reconstructed image in the above-described scattering tomography method are described.

The scattering tomography method according to this embodiment is particularly effective in observing a defective cell in a breast.

As a method of observing a defective cell in a breast, an observation method using x-rays, ultrasonic waves, or MRI has been used. However, the observation using x-rays has the problem that it is difficult to generate a constructed image with x-rays because the tissues through which x-rays pass have a high water content, meaning that x-rays are not suitable for observation of a defective cell in a breast. The observation using ultrasonic waves has an advantage in that ultrasonic waves are easily transmitted through tissues having a high water content, but the problem that ultrasonic waves are heavily damped in lipids which occupies a majority of the region of the tissues and therefore, it is difficult to improve the precision of a constructed image, meaning that ultrasonic waves are not suitable for observation of a defective cell in a breast. The observation using MRI has the problems that a contrast agent is necessary and that although a constructed image can be obtained, it is difficult to determine which is a defective cell from the constructed image, meaning that MRI is not suitable for observation of a defective cell in a breast. In addition, generation of a strong magnetic field requires a superconducting coil and a cooling system for the superconducting coil, and as such, cost is high.

In contrast, 1 GHz to 10 GHz ultrawideband (UWB) microwaves are used for the observation in the scattering tomography method according to this embodiment. Microwaves are effective in observing a defective cell in a breast because the damping of microwaves in a living body, particularly, in lipids and the like, is very small. In addition, its equipment size is smaller than that of MRI, and other substances such as a contrast agent is not necessary, thus allowing for versatile use. Furthermore, in the scattering tomography method according to this embodiment, the above-stated theory of inverse scattering is used to visualize three-dimensional elements in the interior of a living body, such as a breast, on the basis of the multipath (multistatic) scattering wave data of microwaves, thus allowing information on the interior (structure) of a living body to be visualized at high speed and with high precision in a versatile manner.

As examples of the confirmation experiment for the above-described scattering tomography device, the above-stated case filled with margarine and an animal's breast have been observed as living body models.

As an example of the measurement condition, up to 10 GHz microwaves were used as microwaves that are transmitted from the transmitting antenna. In this case, the size of the receiving antenna was set to approximately 4 cm squares. The size of the case was set to approximately 30 cm in base diameter and 10 cm in height. A breast of a pig was observed under this condition, and it was confirmed that a reconstructed image that is more precise than images obtained in the above-mentioned observations using x-rays, ultrasonic waves, and MRI was obtained.

Thus, the scattering tomography method according to this embodiment is particularly effective in observing a defective cell in a breast.

As in the foregoing, in the scattering tomography method according to this embodiment, using an analysis model in which the antenna elements 36 are aligned along the generatrix of the conical body 60a, a partial differential equation for the inverse problem is set, and solving this equation results in a visualization function. With this, in the scattering tomography method of analyzing scattering waves of waves radiated to an object, the information on the interior of an object can be visualized at high speed and with high precision in a versatile manner.

In the multistatic array radar 20, the curvilinear array antenna 37a provided along the generatrix of the conical body 60a rotates about the Z axis of the conical body 60a, and thus $n_x n_y^2$ sets of time-series data are obtained. With $n_t$ time series, the number of data items to be obtained is $n_x n_y^2 n_t$ in total. The information quantity of the $n_x n_y^2 n_t$ data items obtained in this way has $n_y$ times greater redundancy than $n_x n_y n_t$ data items necessary for three-dimensional visualization. Since measurement data has high redundancy as just mentioned, output of the multistatic array radar 20 has high resistance to noise.

Note that the above mathematical expressions and process flow of deriving the mathematical expressions are one example; other mathematical expressions and other deriving process flow may be used Although the microwaves are used as the waves in this embodiment, the microwaves may be replaced by electromagnetic waves or ultrasonic waves in other frequency bands. Furthermore, although periodic waves having a predetermined frequency are used in this embodiment because the microwaves are used, the waves may be pulsed waves instead of the periodic waves.

Furthermore, although the breast is cited as an example of an object in this embodiment, the object is not limited to the breast and may be other objects such as a conical concrete post.

Embodiment 2

Next, Embodiment 2 of the present invention is described.

This embodiment describes the case where a one-dimensional sensor array on a curve is used as a sensor for performing the scattering tomography method. The one-dimensional sensor array includes transmitting antenna elements and receiving antenna elements arranged as a curved line in one dimension (a multi-array antenna).

The configuration of the multistatic array radar 20 serving as a scattering tomography device according to this embodiment is almost the same as that of the multistatic array radar 20 according to Embodiment 1, but is different from that of the multistatic array radar 20 according to Embodiment 1 in that transmitting antenna elements and receiving antenna elements are arranged as a curved line in one dimension. Specifically, the generatrix of the conical body in the conical analysis model in Embodiment 1 is changed into the form of a curved line, and the transmitting antenna elements and the receiving antenna elements are arranged along the resultant curved generatrix. Therefore, the image reconstruction algorithm used by the image reconstructor of the multistatic array radar according to this embodiment is different from that in the multistatic array radar 20 according to Embodiment 1.

Hereinafter, the image reconstruction algorithm in the scattering tomography method according to this embodiment is described.

Image Reconstruction Algorithm

Figure 6:
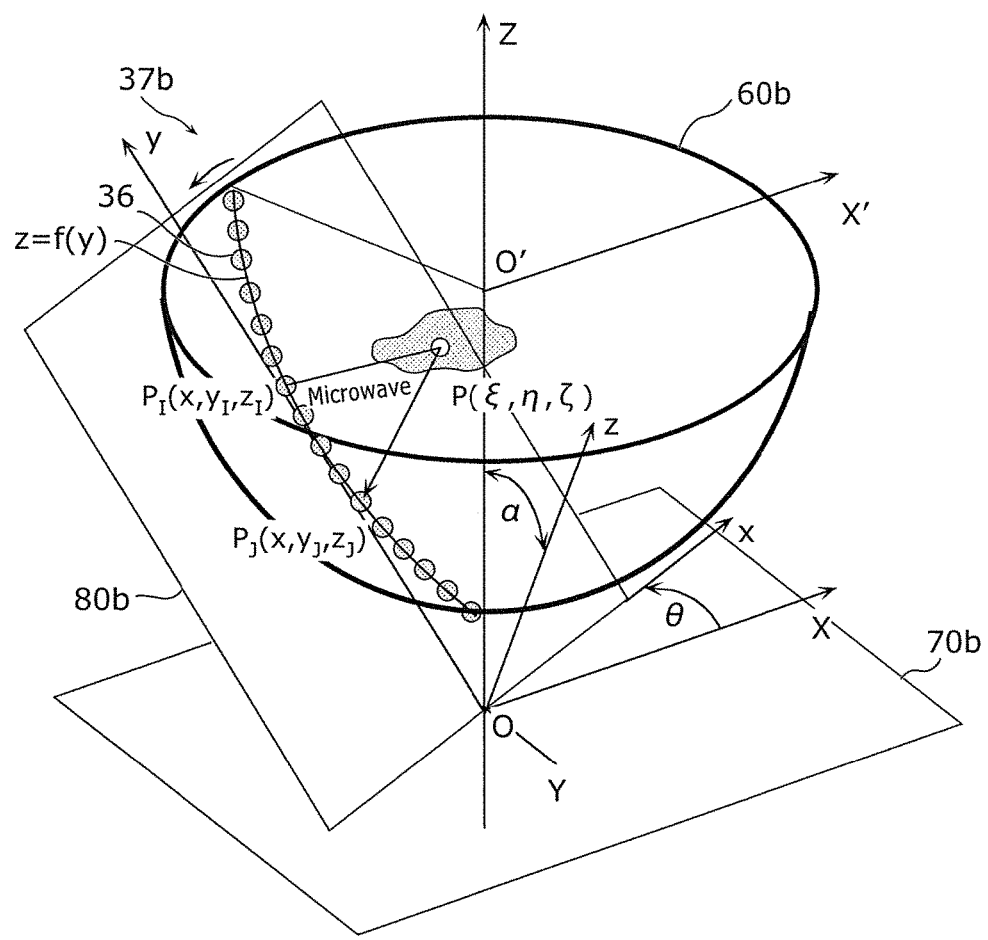
FIG. 6 illustrates an analysis model for explaining a principle of a scattering tomography method according to Embodiment 2.
Figure 7:
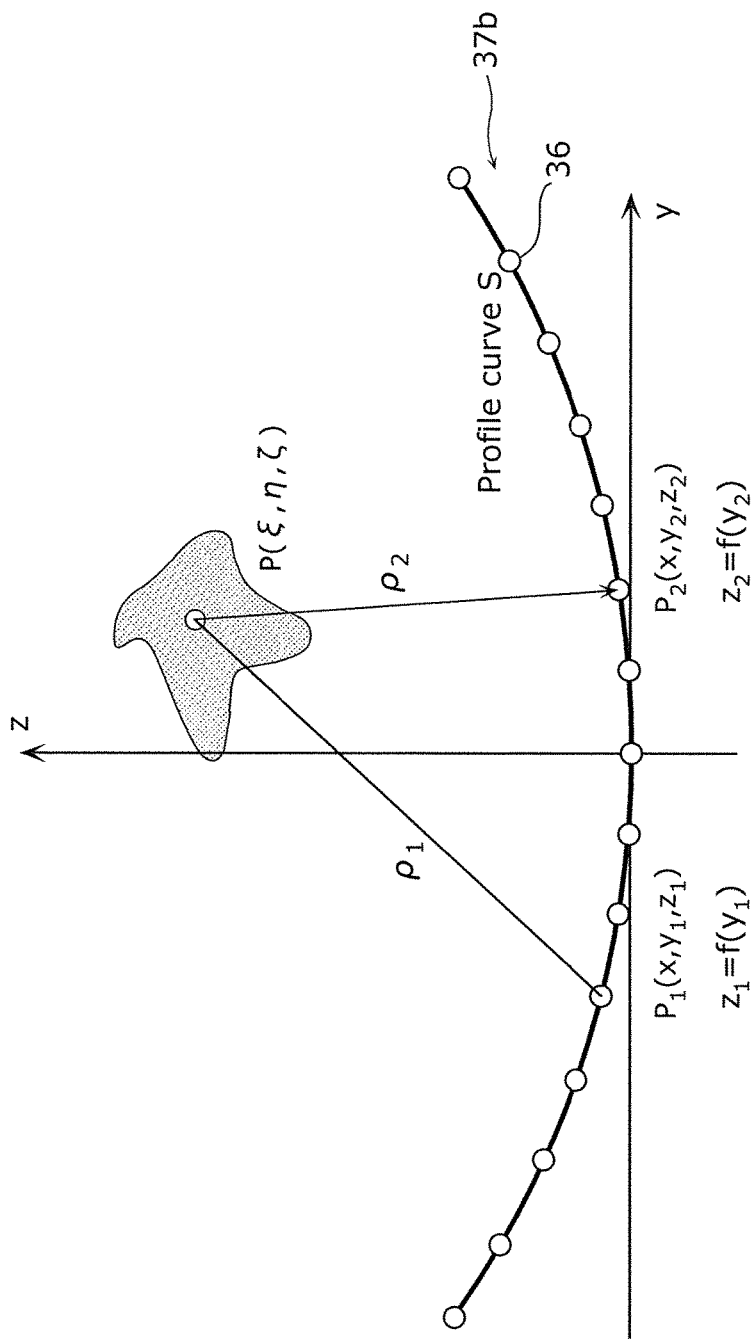
FIG. 7 illustrates an analysis model for explaining a principle of a scattering tomography method according to Embodiment 2.

FIG. 6 and FIG. 7 illustrate an analysis model for explaining a principle of a scattering tomography method according to this embodiment. The following describes derivation of a visualization function that is applied in the case where the model illustrated in FIG. 6 and FIG. 7 is used as an analysis model and the sensor of the multistatic array radar is a one-dimensional sensor array.

In the case of the image reconstruction algorithm (theory) described below, it is assumed that the subject to be visualized is a conical body having a curved generatrix, that is, a semispherical or dome-shaped conical body. This conical body is used as an analysis model, and a wave radiation point (one transmitting antenna element 36a) and a wave receiving point (one receiving antenna element 36b) are arbitrarily arranged on the generatrix. Information on the interior of an object is then visualized using transmitted data representing waves radiated from the wave radiation point and scattered wave data representing scattered waves received at the wave receiving point.

Specifically, the analysis model in this embodiment assumes that the subject to be visualized is a conical body (a substantially conical body) 60b having a curved generatrix as illustrated in FIG. 6. The plurality of antenna elements 36 are arranged along the generatrix of the conical body 60b. The plurality of antenna elements 36 constitute a curvilinear array antenna 37b. In the curvilinear array antenna 37b illustrated in FIG. 6, the curvilinear array antenna 37b rotates about the axis passing through the vertex of the conical body 60b and the center of the base of the conical body 60b. In other words, the curvilinear array antenna 37b including the plurality of transmitting antenna elements 36a and the plurality of receiving antenna elements 36b is provided linearly in the same direction as the axis of rotational symmetry of the case, at least when seen in a plan view from one direction. The axis of rotational symmetry of the case indicates a straight line connecting the vertex of the conical body to the center of the base of the conical body.

More specifically, suppose a tangent plane 80b of the conical body 60b at the position of the curvilinear array antenna 37b, and it is assumed that this virtual tangent plane 80b rotates about the axis passing through the vertex of the conical body 60b and the center of the base of the conical body 60b, and scattered wave data can be obtained for every angle θ of the rotation. A three-dimensional structure of the interior of the conical body 60b is reconstructed from such multistatic times-series data in a surface of the conical body 60b. This theory is described below.

In this analysis model, suppose that the vertex of the conical body 60b is point O, and the center of the circular base of the conical body 60b is point O' as illustrated in FIG. 6. The direction from the point O to the point O' is the Z direction (Z-axis direction). On the side surface of the conical body 60b, the plane contacting the conical body 60b at the position of one curvilinear array antenna 37b is the tangent plane 80b. The plane parallel to the base of conical body 60b and including a point at which this tangent plane 80b intersects with the Z axis is referred to as a reference plane 70b. An arbitrary one direction in the reference plane 70b is the X direction (X-axis direction), and the direction perpendicular to the X direction in the reference plane 70b is the Y direction (Y-axis direction).

In the base of the conical body 60b, the direction parallel to the X direction is referred to as an X' direction (X'-axis direction), and the direction parallel to the Y direction is referred to as a Y' direction (Y'-axis direction).

One direction of the cross line on which this tangent plane 80b and the reference plane 70b interest with each other is the x direction (x-axis direction). On the tangent plane 80b, the direction from the point O toward the base of the conical body 60b is the y direction (y-axis direction). The direction perpendicular to the x direction and the y direction is the z direction (z-axis direction).

On the reference plane 70b, the x axis rotates about the Z axis, and the angle between the X axis and the x axis is denoted by θ. The angle between the Z axis and the z axis is denoted by α.

FIG. 7 is a partially enlarged schematic view of the curvilinear array antenna 37b illustrated in FIG. 6. As illustrated in FIG. 7, the x-coordinate and the y-coordinate are on a surface of an object, and the z-coordinate is along a normal of the surface of the object. In this analysis model, the transmitting antenna elements 36a and the receiving antenna elements 36b are provided on a curved surface in xyz-space.

In the image reconstruction algorithm according to this embodiment, the Green's function necessary for visualization is set first similarly to the scattering tomography method according to Embodiment 1. Next, a partial differential equation in six-dimensional space (t, x, $y_1$, $y_2$, $z_1$, $z_2$) is constructed. The scattering field solution of this partial differential equation is the above Green's function. This partial differential equation is then solved using, as a boundary condition, the transmitted data of waves radiated from the transmitting antenna elements 36a arranged in a curve and the received data of waves received by the receiving antenna elements 36b arranged in the curve, and an exact solution (function) is determined where t→0, x→x, $y_1$→$y_2$ (=y), and $z_2$→$z_1$ (=z). Thus, the visualization function including an exact solution (function) is determined, allowing information on the interior of an object to be visualized at high speed and with high precision in a versatile manner.

A specific example is as follows.

1. Inverse Problem of Scattering and the Green's Function

Suppose a situation where waves radiated from $r_1$ are reflected at a point ξ and travel to a point $r_2$ as in FIG. 6. Under the condition that a frequency ω is constant, the wave transmitting point $r_1$ and the wave receiving point $r_2$ freely move on a curved surface (the side surface of the conical body 60b) while the wave transmitting point $r_1$ and the wave receiving point $r_2$ satisfy a certain constraint. Data obtained in this case is denoted by $G(r_1, r_2, \omega)$. This function relates to distribution of reflection points within a region. At this time, an angular frequency ω=2πf. $G(r_1, r_2, \omega)$ is a sum of reflected signals from all the points ξ. Since there are many reflection points within the region, $G(r_1, r_2, \omega)$ can be thought of as in Expression 1 indicated in Embodiment 1.

Note that in this embodiment, the constraint that restricts the wave transmitting point $r_1$ and the wave receiving point $r_2$ is a condition that the x-coordinate of $r_1$ and the x-coordinate of $r_2$ in the local coordinate system are equal (x is fixed).

A theoretical structure of the inverse problem of scattering is described using this function $G(r_1, r_2, \omega)$).

2. Theory of Multistatic Inverse Scattering on Curved Surface of Rotational Symmetry Using Conical Analysis Model Having Curved Generatrix Hereinafter, a method of determining this differential operator is described. In the analysis mode according to this embodiment, the generatrix of the conical body in the conical analysis model in Embodiment 1 is changed into the form of a curved line, and the transmitting antenna elements and the receiving antenna elements are arranged along the resultant curved generatrix, as illustrated in FIG. 6 and FIG. 7. And the antenna array provided along this curved generatrix rotates about the Z axis. On the curved generatrix, the x-, y-, and z-coordinates of $r_1$ are not necessarily equal to those of $r_2$. Specifically, $r_1=(x, y_1, z_1)$ and $r_2=(x, y_2, z_2)$.

Here, the function G is defined as in Expression 4 indicated in Embodiment 1, and an equation which the function $G(r_1, r_2, \omega)$ satisfies is determined using $r_1=(x_1, y_1, z_1)$ and $r_2=(x_2, y_2, z_2)$. A function φ such as Expression 36 below is introduced as an equation which the function $G(r_1, r_2, \omega)$ satisfies. Note that φ in Expression 36 corresponds to the reconstruction function (the solution) for reconstructing an image relating to information on the interior of an object according to the present invention.

With reference to FIG. 7, suppose a wave radiated from point $P_1$ on a profile curve S, reflected at point P, and received at point $P_2$. The function φ can be written as in Expression 36 below.

[Math. 40]

$$\varphi(x, y_1, y_2, z_1, z_2) = \int\int_D \frac{e^{ik\rho_1}}{\rho_1} \frac{e^{ik\rho_2}}{\rho_2} \varepsilon(\xi, \eta, \zeta) d\xi d\eta d\zeta$$

$$\rho_1 = \sqrt{(x-\xi)^2 + (y_1-\eta)^2 + (z_1-\zeta)^2}$$

$$\rho_2 = \sqrt{(x-\xi)^2 + (y_2-\eta)^2 + (z_2-\zeta)^2}$$

Expression 36

Herein, it is assumed that a time factor is proportional to exp(−iωt), and the wave number is denoted by k. The kernel function in the term to be integrated in the above expression is denoted by φ.

[Math. 41]

$$\phi = \frac{e^{ik\rho_1}}{\rho_1} \frac{e^{ik\rho_2}}{\rho_2}$$

Expression 37

A partial differential equation, the scattering field function of which is this expression or a value obtained by differentiating and integrating this expression with respect to ξ, η, ζ or the like is determined. In order for this to be done, high-order terms may be ignored in calculation for 1/ρ resulting from the differentiation.

Here, an abridged notation for differentiation is defined as in Expression 38 below.

[Math. 42]

$$\frac{\partial}{\partial t} \to \partial_t, \frac{\partial}{\partial x} \to \partial_x, \frac{\partial}{\partial y_1} \to \partial_{y_1},$$

$$\frac{\partial}{\partial y_2} \to \partial_{y_2}, \frac{\partial}{\partial z_1} \to \partial_{z_1}, \frac{\partial}{\partial z_2} \to \partial_{z_2}$$

Expression 38

The orders of Φ are differentiated using Expression 38. Expression 39 below is obtained.

[Math. 43]

$$\partial_x \phi = ik(x-\xi)\left(\frac{1}{\rho_1}+\frac{1}{\rho_2}\right)\phi + o(\rho^{-3})$$

$$\partial_{y_1} \phi = ik\frac{y_1-\eta}{\rho_1}\phi + o(\rho^{-3})$$

$$\partial_{y_2} \phi = ik\frac{y_2-\eta}{\rho_2}\phi + o(\rho^{-3})$$

$$\partial_{z_1} \phi = ik\frac{z_1-\zeta}{\rho_1}\phi + o(\rho^{-3})$$

$$\partial_{z_2} \phi = ik\frac{z_2-\zeta}{\rho_2}\phi + o(\rho^{-3})$$

$$\partial_x \partial_x \phi = (ik)^2(x-\xi)^2\left(\frac{1}{\rho_1}+\frac{1}{\rho_2}\right)^2 \phi + o(\rho^{-3})$$

$$\partial_{y_1} \partial_{y_1} \phi = (ik)^2\left(\frac{y_1-\eta}{\rho_1}\right)^2 \phi + o(\rho^{-3})$$

$$\partial_{y_2} \partial_{y_2} \phi = (ik)^2\left(\frac{y_2-\eta}{\rho_2}\right)^2 \phi + o(\rho^{-3})$$

$$\partial_{z_1} \partial_{z_1} \phi = (ik)^2\left(\frac{z_1-\zeta}{\rho_1}\right)^2 \phi + o(\rho^{-3})$$

$$\partial_{z_2} \partial_{z_2} \phi = (ik)^2\left(\frac{z_2-\zeta}{\rho_2}\right)^2 \phi + o(\rho^{-3})$$

Expression 39

In the expressions below, the terms o(*), which are complicated, are omitted. Note that * means an arbitrary variable. The sum of four expressions involving the second order differential is as in Expression 40 below.

[Math. 44]

$$\Delta_5 \phi = \left(\partial_x^2 + \partial_{y_1}^2 + \partial_{y_2}^2 + \partial_{z_1}^2 + \partial_{z_2}^2\right)\phi$$

$$= (ik)^2 \left\{2 + 2\frac{(x-\xi)^2}{\rho_1 \rho_2}\right\}\phi$$

Expression 40

Therefore:

[Math. 45]

$$\{\Delta_5 - 2(ik)^2\}\phi = 2(ik)^2 \frac{\rho_1^2 - (y_1-\eta)^2 - (z_1-\zeta)^2}{\rho_1 \rho_2}$$

$$= 2(ik)^2 \frac{\rho_2^2 - (y_2-\eta)^2 - (z_2-\zeta)^2}{\rho_1 \rho_2}$$

Expression 41

Operating the operator in the left side of Expression 41 twice leads to Expression 42 below.

[Math. 46]

$$\{\Delta_5 - 2(ik)^2\}^2 \phi = 4(ik)^4 \frac{\{\rho_1^2 - (y_1-\eta)^2 - (z_1-\zeta)^2\}\{\rho_2^2 - (y_2-\eta)^2 - (z_2-\zeta)^2\}}{\rho_1^2 \rho_2^2}$$

$$= 4(ik)^4 \{1 - (ik)^{-2}\partial_{y_1}^2 - (ik)^{-2}\partial_{z_1}^2\}\{1 - (ik)^{-2}\partial_{y_2}^2 - (ik)^{-2}\partial_{z_2}^2\}\phi$$

Expression 42

Thus, φ satisfies the equation in Expression 43 below.
[Math. 47]

$$[\tfrac{1}{4}\{\Delta_5 - 2(ik)^2\}^2 - (ik)^4\{1-(ik)^{-2}\partial_{y_1}^2-(ik)^{-2}\partial_{z_1}^2\}\{1-(ik)^{-2}\partial_{y_2}^2-(ik)^{-2}\partial_{z_2}^2\}]\phi = 0$$

Expression 43

This is reorganized into the equation in Expression 44 below.
[Math. 48]

$$[\tfrac{1}{4}\Delta_5^2 - (ik)^2\partial_x^2 - (\partial_{y_1}^2+\partial_{z_1}^2)(\partial_{y_2}^2+\partial_{z_2}^2)]\phi = 0$$

Expression 44

Although a steady-state case is assumed in derivation of Expression 44, it is easy to extend Expression 44 to an unsteady-state case. In order to extend Expression 44 to an unsteady-state case, a variable in Expression 44 is replaced as in Expression 45 below.

[Math. 49]

$$-ik \rightarrow \frac{1}{c}\partial_t$$

Expression 45

This leads to Expression 46 below in the end. Note that Expression 46 corresponds to a scattering field equation according to the present invention.

[Math. 50]

$$\left[\frac{1}{4}\Delta_5^2 - \frac{1}{c^2}\partial_t^2\partial_x^2 - \left(\partial_{y_1}^2+\partial_{z_1}^2\right)\left(\partial_{y_2}^2+\partial_{z_2}^2\right)\right]\phi = 0$$

Expression 46

Assuming that a time factor of φ is proportional to exp(−iωt), a solution of Expression 46 is determined. First, the multi-dimensional Fourier transform of φ with respect to t, x, $y_1$, and $y_2$ results in Expression 47 below.

[Math. 51]

$$\tilde{\phi}(k_x, k_{y_1}, k_{y_2}, z_1, z_2, \omega) = \int_{-\infty}^{\infty} e^{i\omega t} dt \int_{-\infty}^{\infty} e^{ik_{y_1} y_1} dy_1$$

$$\int_{-\infty}^{\infty} e^{ik_{y_2} y_2} dy_2 \int_{-\infty}^{\infty} e^{ik_x x} \phi(x, y_1, y_2, z_1, z_2, t) dx$$

Expression 47

Assuming that a partial differential with respect to $z_1$ and a partial differential with respect to $z_2$ are $D_{z_1}$ and $D_{z_2}$, respectively, Expression 48 below is obtained.
[Math. 52]

$$\{(D_{z_1}^2+D_{z_2}^2-k_x^2-k_{y_1}^2-k_{y_2}^2)^2 - 4k^2k_x^2 - 4(D_{z_1}^2-k_{y_1}^2)(D_{z_2}^2-k_{y_2}^2)\}\tilde{\phi}=0$$

Expression 48

This equation, which is to be solved, has two variables $z_1$ and $z_2$. Therefore, a boundary value problem cannot be obtained unless a boundary condition for fixed (x, $y_1$, $y_2$) or ($k_x$, $k_{y_1}$, $k_{y_2}$) is given in a one-dimensional, flexible region within ($z_1$, $z_2$) space. However, a boundary condition obtained by measurement with the radar is that only given at one point (f($y_1$), f($y_2$)) within the ($z_1$, $z_2$) space.

In order to solve this important problem, the following requirement is given. Consistency is required between the theory in the present section and the theory in the local tangent plane described in the previous section. This includes a special case where $z_1=z$ and $z_2=z$ in the theory in the present section in which $z_1$ and $z_2$ are independent.

Assume that a solution of Expression 48 is Expression 49 below.

[Math. 53]

$$E(k_x, k_{y_1}, k_{y_2}, z_1, z_2) = \exp(is_1 z_1)\exp(is_2 z_2) \qquad \text{Expression 49}$$

When $z_1=z_2=z$, this becomes Expression 50 below.

[Math. 54]

$$E(k_x, k_{y_1}, k_{y_2}, z_1, z_2) = \exp\{i(s_1+s_2)z\} \qquad \text{Expression 50}$$

Substituting Expression 49 into Expression 48 gives the following expression.

[Math. 55]

$$(s_1^2 + s_2^2 + k_x^2 + k_{y_1}^2 + k_{y_2}^2)^2 - 4k^2 k_x^2 - 4(s_1^2 + k_{y_1}^2)(s_2^2 + k_{y_2}^2) = 0 \qquad \text{Expression 51}$$

Furthermore, another equation is necessary. Here, the above-mentioned consistency requirement leads to the following.

[Math. 56]

$$s_1 + s_2 = \sqrt{\left(\sqrt{k^2 - k_{y_1}^2} + \sqrt{k^2 - k_{y_2}^2}\right)^2 - k_x^2} \qquad \text{Expression 52}$$

Using Expression 51 and Expression 52, $s_1(k_x, k_{y_1}, k_{y_2})$ and $s_2(k_x, k_{y_1}, k_{y_2})$ are determined to be those in Expression 53 below.

[Math. 57]

$$s_1(k_x, k_{y_1}, k_{y_2}) = \frac{\sqrt{k^2 - k_{y_1}^2}\sqrt{\left(\sqrt{k^2 - k_{y_1}^2} + \sqrt{k^2 - k_{y_2}^2}\right)^2 - k_x^2}}{\sqrt{k^2 - k_{y_1}^2} + \sqrt{k^2 - k_{y_2}^2}}$$

$$s_2(k_x, k_{y_1}, k_{y_2}) = \frac{\sqrt{k^2 - k_{y_2}^2}\sqrt{\left(\sqrt{k^2 - k_{y_1}^2} + \sqrt{k^2 - k_{y_2}^2}\right)^2 - k_x^2}}{\sqrt{k^2 - k_{y_1}^2} + \sqrt{k^2 - k_{y_2}^2}}$$

Expression 53

A specific process of the calculation is performed later. A solution of the equation in Expression 46 can be written as Expression 54 below using these $s_1(k_x, k_{y_1}, k_{y_2})$ and $s_2(k_x, k_{y_1}, k_{y_2})$.

[Math. 58]

$$\phi(x, y_1, y_2, z_1, z_2, k) = \qquad \text{Expression 54}$$

$$\frac{1}{(2\pi)^3} \int_{-\infty}^{\infty} \int_{-\infty}^{\infty} \int_{-\infty}^{\infty} e^{-i(k_x x + k_{y_1} y_1 + k_{y_2} y_2)} a(k_x, k_{y_1}, k_{y_2})$$

$$e^{is_1(k_x, k_{y_1}, k_{y_2})z_1} e^{is_2(k_x, k_{y_1}, k_{y_2})z_2} dk_x dk_{y_1} dk_{y_2}$$

Assume that an equation of the profile curve S with x fixed is Expression 55 below.

[Math. 59]

$$z = f(y) \qquad \text{Expression 55}$$

The boundary condition given on the profile curve S is Expression 56 below.

[Math. 60]

$$\phi(x, y_1, y_2, f(y_1), f(y_2), k) = \qquad \text{Expression 56}$$

$$\frac{1}{(2\pi)^3} \int_{-\infty}^{\infty} \int_{-\infty}^{\infty} \int_{-\infty}^{\infty} e^{-i(k_x x + k_{y_1} y_1 + k_{y_2} y_2)} a(k_x, k_{y_1}, k_{y_2})$$

$$e^{i\{s_1(k_x, k_{y_1}, k_{y_2})f(y_1) + s_2(k_x, k_{y_1}, k_{y_2})f(y_2)\}} dk_x dk_{y_1} dk_{y_2}$$

This equation is used to determine $a(k_x, k_{y_1}, k_{y_2})$. The abridged notations below are used.

[Math. 61]

$$a(k) = a(k_x, k_{y_1}, k_{y_2})$$

$$s_1(k) = s_1(k_x, k_{y_1}, k_{y_2})$$

$$s_2(k) = s_2(k_x, k_{y_1}, k_{y_2}) \qquad \text{Expression 57}$$

Expression 54 becomes an integral equation with respect to $a(k_x, k_{y_1}, k_{y_2})$ as indicated below.

[Math. 62]

$$\phi(x, y_1, y_2, f(y_1), f(y_2), k) = \qquad \text{Expression 58}$$

$$\frac{1}{(2\pi)^3} \int_{-\infty}^{\infty} \int_{-\infty}^{\infty} \int_{-\infty}^{\infty} e^{-i(k_x x + k_{y_1} y_1 + k_{y_2} y_2)} a(k) e^{i\{s_1(k)f(y_1) + s_2(k)f(y_2)\}} dk$$

If $a(k)$ can be determined from Expression 58, assume $z_1=z_2=z$ in Expression 59 below, and then this expression is Fourier transformed with respect to k. Thus, the visualization function is determined. The visualization function in the local coordinate system is determined as in Expression 60 below.

[Math. 63]

$$\phi(x, y_1, y_2, z_1, z_2, k) = \qquad \text{Expression 59}$$

$$\frac{1}{(2\pi)^3} \int_{-\infty}^{\infty} \int_{-\infty}^{\infty} \int_{-\infty}^{\infty} e^{-i(k_x x + k_{y_1} y_1 + k_{y_2} y_2)} a(k) e^{is_1(k)z_1} e^{is_2(k)z_2} dk$$

[Math. 64]

$$\rho(r) = \lim_{t \to 0} \left[ \frac{1}{2\pi} \int_{-\infty}^{\infty} \phi(x, y, y, z, zk) e^{ickt} dk \right] \qquad \text{Expression 60}$$

Here, a solution of the integral equation in Expression 58 is determined. Time-series data $\varphi(x, y_I, y_J, z_I, z_J, t)$ measured at points $P_I$ and $P_J$ on the curved surface is Fourier transformed into $\Phi(k_x, y_I, y_J, k)$ which can be written as follows.

[Math. 65]

$$\Phi_{I,J}(k_x, y_I, y_J, k) = \int_{-\infty}^{\infty}\int_{-\infty}^{\infty} e^{ikt-ik_x x}\phi(x, y_I, y_J, z_I, z_J, t)dtdx \quad \text{Expression 61}$$

Here, $z_I$ and $z_J$ satisfy the expression below.

[Math. 66]

$$z_I = f(y_I)$$
$$z_J = f(y_J) \quad \text{Expression 62}$$

Furthermore, except when x=0, there is no data, and therefore φ can be written as follows.

[Math. 67]

$$\phi(x, y_I, y_J, z_I, z_J, t) = \delta(x)\phi_R(y_I, y_J, z_I, z_J, t) \quad \text{Expression 63}$$

Then, Expression 61 becomes the following.

[Math. 68]

$$\Phi_{I,J}(k_x, y_I, y_J, k) = \int_{-\infty}^{\infty}\int_{-\infty}^{\infty} e^{ikt-ik_x x}\delta(x)\phi_R(y_I, y_J, z_I, z_J, t)dtdx$$
$$= \int_{-\infty}^{\infty} e^{-ikt}\phi_R(y_I, y_J, z_I, z_J, t)dt \quad \text{Expression 64}$$

The right side of Expression 64 does not include kx. However, considering that this is data at a certain angle θ, the right side is represented by the function in Expression 65 below.

[Math. 69]

$$\Psi_{I,J}(y_I, y_J, k, \theta) = \int_{-\infty}^{\infty} e^{-ikt}\phi_{RE}(y_I, y_J, z_I, z_J, t)dt \quad \text{Expression 65}$$

With the use of this sign, Expression 66 below is obtained from Expression 58.

[Math. 70]

$$\Psi_{I,J}(y_I, y_J, k, \theta) = \quad \text{Expression 66}$$
$$\frac{1}{(2\pi)^2}\int_{-\infty}^{\infty}\int_{-\infty}^{\infty} e^{-i(k_{y_1}y_1+k_{y_2}y_2)}a_{I,J}(k_x, k_{y_1}, k_{y_2}, k)$$
$$e^{i\{s_1(k)z_I+s_2(k)z_J\}}dk_{y_1}dk_{y_2}$$

Expression 66 is rewritten into Expression 67 below.

[Math. 71]

$$\Psi_{I,J}(y_I, y_J, k, \theta)\delta(y_1-y_I)\delta(y_2-y_J)\delta(x) = \quad \text{Expression 67}$$
$$\frac{1}{(2\pi)^3}\int_{-\infty}^{\infty}\int_{-\infty}^{\infty}\int_{-\infty}^{\infty} e^{i(k_x x+k_{y_1}y_1+k_{y_2}y_2)}a_{I,J}(k_x, k_{y_1}, k_{y_2}, k)$$
$$e^{i\{s_1(k)z_I+s_2(k)z_J\}}dk_x dk_{y_1}dk_{y_2}$$

The Fourier transforms on the both sides are removed, resulting in Expression 68.

[Math. 72]

$$\int\int\int_{-\infty}^{\infty} e^{i(k'_x x+k'_{y_1}y_1+k'_{y_2}y_2)}\Psi_{I,J}(y_I, y_J, k, \theta) \quad \text{Expression 68}$$
$$\delta(y_1-y_I)\delta(y_2-y_J)\delta(x)dxdy_1dy_2 =$$
$$\int\int\int_{-\infty}^{\infty} e^{i(k'_x x+k'_{y_1}y_1+k'_{y_2}y_2)}$$
$$\left\{\frac{1}{(2\pi)^3}\int\int\int_{-\infty}^{\infty} e^{-i(k_x x+k_{y_1}y_1+k_{y_2}y_2)}\right.$$
$$\left. a_{I,J}(k_x, k_{y_1}, k_{y_2}, k)e^{i\{s_1(k)z_I+s_2(k)z_J\}}\right.$$
$$\left. dk_x dk_{y_1}dk_{y_2}\right\}\delta xdy_1dy_2$$

Integrating this gives:

[Math. 73]

$$e^{i(k'_{y_1}y_I+k'_{y_2}y_J)}\Psi_{I,J}(y_I, y_J, k, \theta) = \quad \text{Expression 69}$$
$$\int\int\int_{-\infty}^{\infty}\delta(k_x-k'_x)\delta(k_{y_1}-k'_{y_1})\delta(k_{y_2}-k'_{y_2})\cdot$$
$$a_{I,J}(k_x, k_{y_1}, k_{y_2}, k)e^{i\{s_1(k)z_I+s_2(k)z_J\}}dk_x dk_{y_1}dk_{y_2}$$

Integrating this gives Expression 70 below.

[Math. 74]

$$e^{i(k_{y_1}y_I+k_{y_2}y_J)}\Psi_{I,J}(y_I, y_J, k, \theta) =$$
$$a_{I,J}(k_x, k_{y_1}, k_{y_2}, k)e^{i\{s_1(k)z_I+s_2(k)z_J\}} \quad \text{Expression 70}$$

Here, [Math. 75] is obtained as in Expression 71 below.

[Math. 75]

$$a(k_x, k_{y_1}, k_{y_2}, k)$$

[Math. 76]

$$a_{I,J}(k_x, k_{y_1}, k_{y_2}, k) =$$
$$e^{i(k_{y_1}y_I+k_{y_2}y_J)}e^{-i\{s_1(k)z_I+s_2(k)z_J\}}\Psi_{I,J}(y_I, y_J, k, \theta) \quad \text{Expression 71}$$

Furthermore, the sum is determined with respect to every I and J, and thus Expression 72 below is obtained.

[Math. 77]

$$a_\theta(k_x, k_{y_1}, k_{y_2}, k) = \quad \text{Expression 72}$$
$$\sum_{I,J} e^{i(k_{y_1}y_I+k_{y_2}y_J)}e^{-i\{s_1(k)z_I+s_2(k)z_J\}}\Psi_{I,J}(y_I, y_J, k, \theta)$$

A solution of Expression 46, which is a partial differential equation, is as in Expression 73 below.

[Math. 78]

$$\phi(x, y_1, y_2, z_1, z_2, k) = \frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a_\theta(k_x, k_{y_1}, k_{y_2}, k) e^{i s_1(k) z_1} e^{i s_2(k) z_2} dk_x dk_{y_1} dk_{y_2}$$

Expression 73

Assume $y_1 \to y$, $y_2 \to y$ and $z_1 = z_2 = z$ in Expression 73, and thus the visualization function becomes Expression 74 below.

[Math. 79]

$$\phi(x, y, y, z, z, k) = \lim_{y_1 \to y} \left[ \frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a_\theta(k_x, k_{y_1}, k_{y_2}, k) e^{i\{s_1(k) + s_2(k)\}z} dk_x dk_{y_1} dk_{y_2} \right]$$

$$= \lim_{y_1 \to y} \left[ \frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a_\theta(k_x, k_{y_1}, k_{y_2}, k) e^{iz\left\{ \left(\sqrt{k^2 - k_{y_1}^2} + \sqrt{k^2 - k_{y_2}^2}\right)^2 - k_x^2 \right\}^{1/2}} dk_x dk_{y_1} dk_{y_2} \right]$$

Expression 74

Further deforming gives Expression 75 below.

[Math. 80]

$$\rho(x, y, z, \theta) = \int_{-\infty}^{\infty} \phi(x, y, y, z, zk) dk$$

$$= \int_{-\infty}^{\infty} \lim_{y_1 \to y} \left[ \frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a_\theta(k_x, k_{y_1}, k_{y_2}, k) e^{i\{s_1(k) + s_2(k)\}z} dk_x dk_{y_1} dk_{y_2} \right] dk$$

$$= \int_{-\infty}^{\infty} \lim_{y_1 \to y} \left[ \frac{1}{(2\pi)^3} \int_{-\infty}^{\infty}\int_{-\infty}^{\infty}\int_{-\infty}^{\infty} e^{-i(k_x x + k_{y_1} y_1 + k_{y_2} y_2)} a_\theta(k_x, k_{y_1}, k_{y_2}, k) e^{iz\left\{\left(\sqrt{k^2 - k_{y_1}^2} + \sqrt{k^2 - k_{y_2}^2}\right)^2 - k_x^2\right\}^{1/2}} dk_x dk_{y_1} dk_{y_2} \right] dk$$

$$= \lim_{y_1 \to y} \left[ \frac{1}{(2\pi)^3} \int_{-\infty}^{\infty}\int_{-\infty}^{\infty}\int_{-\infty}^{\infty}\int_{-\infty}^{\infty} e^{-i(k_x x + k_{y_1} y_1 + k_{y_2} y_2)} a_\theta(k_x, k_{y_1}, k_{y_2}, k) \left(\frac{dk}{dk_z}\right) dk_x dk_{y_1} dk_{y_2} dk_z \right]$$

Expression 75

The results obtained at angles $\theta$ are integrated, leading to the three-dimensional reconstructed image represented by Expression 76 below.

[Math. 81]

$$P(X, Y, Z) = \int_0^{2\pi} \rho(x, y, z, \theta) d\theta$$

Expression 76

Here, the result of calculation in the tangent space is transformed into the global coordinate system (X, Y, Z). Assuming that the projection of the y-axis onto the (X, Y) plane is y', Expression 77 below holds.

[Math. 82]

$$y = y' \cos \alpha + Z \sin \alpha$$

$$z = -y' \sin \alpha + Z \cos \alpha$$

Expression 77

Expression 78 below represents further transformation from (x, y') to (X, Y).

[Math. 83]

$$x = X \cos \theta + Y \sin \theta$$

$$y = -X \cos \alpha \sin \theta + Y \cos \alpha \cos \theta + Z \sin \alpha$$

$$z = X \sin \alpha \sin \theta - Y \sin \alpha \cos \theta + Z \cos \alpha$$

Expression 78

These transformation formulae are applied to Expression 79 below.

[Math. 84]

$$\rho(x, y, z, \theta) = \frac{1}{(2\pi)^3} \int_{-\infty}^{\infty}\int_{-\infty}^{\infty}\int_{-\infty}^{\infty}\int_{-\infty}^{\infty} e^{-i(k_x x + k_{y_1} y + k_{y_2} y)} a_\theta(k_x, k_{y_1}, k_{y_2}, k) \left(\frac{dk}{dk_z}\right) dk_x dk_{y_1} dk_{y_2} dk_z$$

Expression 79

Furthermore, the variables in Expression 80 below are introduced.

[Math. 85]

$$k_{ye} = k_{y_1} + k_{y_2}$$

$$k_{yo} = k_{y_1} - k_{y_2}$$

Expression 80

Expression 79 above results in Expression 81 below.

[Math. 86]

$$\rho(x, y, z, \theta) = \frac{1}{2(2\pi)^3} \lim_{y_o \to 0} \int_{-\infty}^{\infty}\int_{-\infty}^{\infty}\int_{-\infty}^{\infty}\int_{-\infty}^{\infty} e^{-i(k_x x + k_{ye} y + k_{yo} y_o - k_z z)} a_\theta(k_x, k_{y_1}, k_{y_2}, k)\left(\frac{dk}{dk_z}\right) dk_x dk_{ye} dk_{yo} dk_z$$

Expression 81

Furthermore, the variable transformation (the inverse transformation) in Expression 82 below is performed in a region of the spectrum.

Note that the variables ξ, η, and ζ in Expression 82 and Expression 83 below are different from the coordinates of point P (ξ, η, ζ) in FIG. 7, Expression 36, etc.; they are new variables used for the variable transformation.

[Math. 87]

$$\xi = -k_x \cos\theta + (k_{ye}\cos\alpha + k_z \sin\alpha)\sin\theta$$

$$\eta = -k_x \sin\theta - (k_{ye}\cos\alpha + k_z \sin\alpha)\cos\theta$$

$$\zeta = -k_{ye}\sin\alpha + k_z \cos\alpha \quad \text{Expression 82}$$

The inverse transformation for Expression 82 is given by Expression 83.

[Math. 88]

$$k_x = -\xi\cos\theta - \eta\sin\theta$$

$$k_{ye} = (\xi\sin\theta - \eta\cos\theta)\cos\alpha - \zeta\sin\alpha$$

$$k_z = (\xi\sin\theta - \eta\cos\theta)\sin\alpha + \zeta\cos\alpha \quad \text{Expression 83}$$

The reconstruction function at the angle θ is represented as in Expression 84 below.

[Math. 89]

$$\rho(x, y, z, \theta) = \frac{1}{2(2\pi)^3}\lim_{y_o \to 0}\int_{-\infty}^{\infty}\int_{-\infty}^{\infty}\int_{-\infty}^{\infty}\int_{-\infty}^{\infty} e^{i(\xi X + \eta Y + k_{yo} y_o + \zeta Z)} a_0(k_x, k_{y_1}, k_{y_2}, k)\left(\frac{dk}{dk_z}\right) dk_x dk_{ye} dk_{yo} dk_z$$

$$= \frac{1}{2(2\pi)^3}\lim_{y_o \to 0}\int_{-\infty}^{\infty}\int_{-\infty}^{\infty}\int_{-\infty}^{\infty}\int_{-\infty}^{\infty} e^{i(\xi X + \eta Y + k_{yo} y_o + \zeta Z)} a_0(k_x, k_{y_1}, k_{y_2}, k)\left(\frac{dk}{dk_z}\right) d\xi d\eta dk_{yo} d\zeta$$

Expression 84

The function in the term to be integrated is as in Expression 85 below.

[Math. 90]

$$a_\theta(k_x, k_{y_1}, k_{y_2}, k) =$$

$$\sum_{I,J} e^{i(k_{y_1} y_I + k_{y_2} y_J)} e^{-i[s_1(k)z_I + s_2(k)z_J]} \Psi_{I,J}(y_I, y_J, k, \theta)\frac{dk}{dk_z} =$$

$$\frac{k_z\sqrt{k^2 - k_{y_1}^2}\sqrt{k^2 - k_{y_2}^2}}{k(k_x^2 + k_z^2)}$$

Expression 85

Here, since $k_x$, $k_{y_1}$, $k_{y_2}$, and $k_z$ are functions of ξ, η, ζ, and $k_{yo}$ as in Expression 30 and Expression 33, it is possible to transform the data in the local coordinates at the angle θ into data in the global coordinates by using the Fourier transform only. Expression 86 below is used for the transformation into data in the global coordinates. In other words, the integration with respect to the angle θ in the end results in the visualization function.

[Math. 91]

$$P(X, Y, Z) = \int_0^{2\pi} \rho(x, y, z, \theta) d\theta \quad \text{Expression 86}$$

This visualization function is used to reconstruct an image relating to information on the interior of an object. Thus, it is possible to visualize or image information on the interior of an object, such as a flaw inside the object, in a versatile manner at high speed and with high precision. Furthermore, since the function φ is set for a three-dimensional space in the reconstructing, information on the interior of an object having a curved surface with high curvature can be more accurately visualized at high speed.

As described above, in the scattering tomography method according to this embodiment, a partial differential equation for the inverse problem is set in an analysis model in which a sensor is arranged arbitrarily on a curved surface, and solving this equation results in a visualization function. With this, in the scattering tomography method of analyzing scattering waves of waves radiated to an object, the information on the interior of an object having a curved surface with high curvature can be visualized at high speed in a versatile manner.

Particularly, this embodiment derives a visualization function in the scattering tomography method that is applied in the case where the sensor of the multistatic array radar is a curved one-dimensional sensor array. Therefore, with this visualization function, a reconstructed image can be obtained through the measurement performed on a wider plane of rotational symmetry than that in the case described in Embodiment 1 where the sensor of the multistatic array radar is one-dimensional sensor array.

Embodiment 3

Next, Embodiment 3 of the present invention is described. This embodiment describes mammography equipment as an example of the scattering tomography apparatus that uses the antenna system 100 including an ultrawideband antenna as the sensor 30 in the multistatic array radar 20 described in Embodiments 1 and 2.

Generally, a wideband antenna includes conductor patterns formed on the front and rear surfaces of a dielectric substrate. Specifically, one pair of antenna elements including copper foil conductor patterns are symmetrically arranged on a surface of a dielectric substrate. The pair of antenna elements are connected to a coaxial line via a balun such as a multilayer balun provided on the dielectric substrate.

Here, the balun means a balanced/unbalanced converter, which is an element for converting electric signals between balanced and unbalanced states. For example, the balun is used to connect a completely balanced (electrically symmetrical) antenna, such as a dipole antenna, to a coaxial cable in an unbalanced state.

A balun for use in the frequency band of 5 GHz or less usually uses a coil transducer. It is, however, difficult to manufacture a coil transducer that supports a higher frequency band, for example, the high frequency band of 10 GHz or more, due to issues related to the number of turns, the size, etc., of a coil; therefore, it is difficult to provide a balun that supports a high frequency band. For this reason, it is unlikely that a balun is used to provide an antenna that supports a wide band including the ultrawideband (USB).

The antenna system 100 described below is capable of transmitting a signal to an antenna element without using a balun; thus, it is possible to provide an antenna that supports a wide band including the UWB. Consequently, it is possible to provide accurate mammography equipment which operates at high speed and supports the frequency band that is not limited by the number of turns and the size of a coil by using an ultrawide frequency band.

First, the configuration of the antenna system 100 according to this embodiment is described. The mammography equipment described above transmits microwave signals which are high-frequency signals to an examination subject which is a breast of a living body, and receives scattered wave data of reflected signals.

Figure 8:
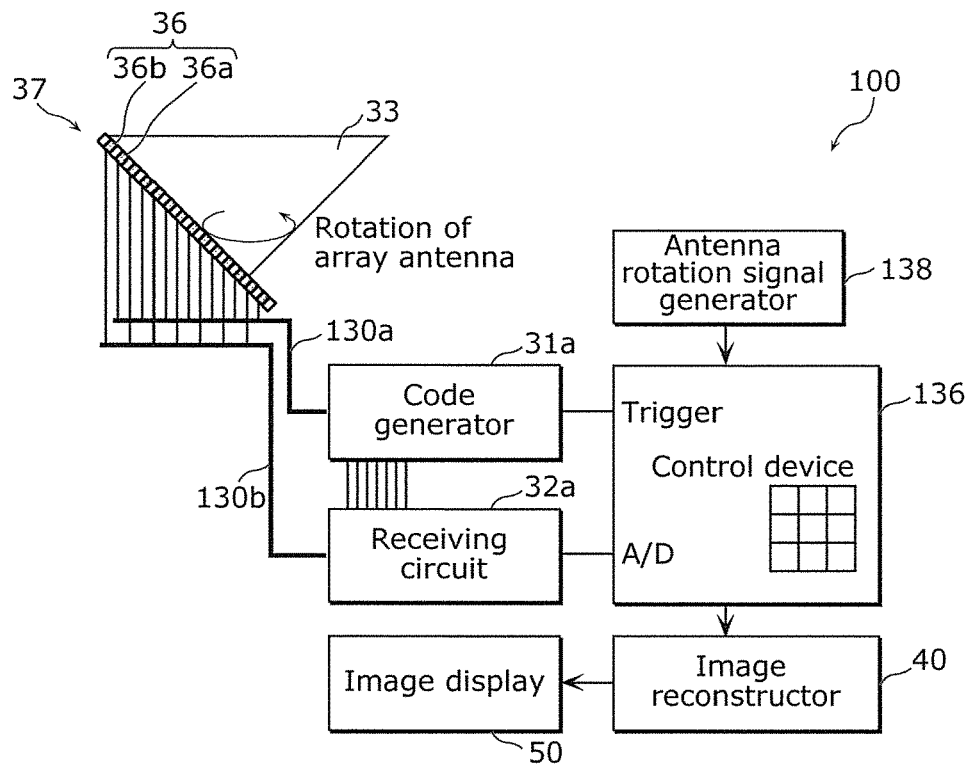
FIG. 8 schematically illustrates a configuration of an antenna system according to Embodiment 3.

FIG. 8 schematically illustrates the configuration of the antenna system 100.

As illustrated in FIG. 8, the antenna system 100 according to this embodiment includes an array antenna 37 that transmits waves, such as microwaves, to an examination subject placed in the case 33, a code generator 31a, a receiving circuit 32a, a control device 136, an antenna rotation signal generator 138, the image reconstructor 40, and the image display 50.

The array antenna 37 includes the plurality of transmitting antenna elements 36a and the plurality of receiving antenna elements 36b as illustrated in FIG. 8. The transmitting antenna elements 36a and the receiving antenna elements 36b are alternately arranged in a straight line. Note that the transmitting antenna elements 36a and the receiving antenna elements 36b are not limited to being alternately arranged in a straight line; as an alternative arrangement, a transmitting array antenna in which only the transmitting antenna elements 36a are arranged in a straight line and a receiving array antenna in which only the receiving antenna elements 36b are arranged in a straight line may be arranged in parallel.

As illustrated in FIG. 8, the array antenna 37 is provided along the generatrix of the substantially conical shape of the case 33 having a substantially conical shape inside which a breast which is an examination subject is placed, for example. The array antenna 37 rotates around the case 33 about the vertex of the conical shape of the case 33. At this time, the transmitting antenna elements 36a in the array antenna 37 at each predetermined angle of the rotation transmit waves to the examination subject placed in the case 33.

The receiving antenna elements 36b receive signals that form scattered waved data corresponding to living body information on the examination subject placed inside the case 33, which is to be described later. The receiving antenna elements 36b obtain scattered wave data called multistatic scattered data, for example.

The transmitting antenna elements 36a are connected to the code generator 31a through a coaxial cable 130a. The receiving antenna elements 36b are connected to the receiving circuit 32a through a coaxial cable 130b.

The code generator 31a is an N-channel code generator and includes a field-programmable gate array (FPGA). The code generator 31a transmits, to the transmitting antenna elements 36a, coded signals which are radio frequency (RF) signals from the control device 136, which is to be described later. The signals (RF signals) input to the transmitting antenna elements 36a are a digital code sequence. Switches embedded in the code generator 31a including the FPGA allow the transmitting antenna elements 36a to be selected one by one (channel by channel) in sequence to transmit signals. Note that the code generator 31a is included in the transmitter 31 described in Embodiment 1. The transmitter 31 may include the code generator 31a only or may include other elements together with the code generator 31a.

The receiving circuit 32a is an N-channel receiving circuit. At each predetermined angle of rotation of the array antenna 37, the receiving circuit 32a obtains wave signals that form scattered wave data called multistatic scattered data from the receiving antenna elements 36b included in the array antenna 37. Note that the receiving circuit 32a is included in the receiver 32 described in Embodiment 1.

The code generator 31a and the receiving circuit 32a correspond to the signal generator and the receiver according to the present invention, respectively.

The control device 136 controls the signals to be transmitted to the code generator 31a and converts the signals received by the receiving circuit 32a into scattered wave data. The control device 136 is configured of a computer, for example. Note that the control device 136 may include a calculator, an analog-to-digital (A/D) converter, a memory, or the like other than a computer.

The antenna rotation signal generator 138 generates antenna rotation signals for rotating the array antenna 37 through each predetermined angle of rotation. The antenna rotation signal generator 138 transmits the generated antenna rotation signals to the control device 136. The control device 136 gives the antenna rotation signals to the array antenna 37. With this, the array antenna 37 rotates around the case 33.

The image reconstructor 40 is a part for performing a mathematical method called scattering tomography. The scattering tomography is a (scattering tomography) method of visualizing information on the interior of an object by observing and analyzing scattered waves resulting from waves being radiated to the object by using a so-called inverse problem. The image reconstructor 40 generates a visualizing signal for visualizing information on the interior of the examination subject placed in the case 33 from the scattered wave data transmitted from the control device 136.

In order to visualize information on the interior of an object having a flexible shape, such as a living body, it is necessary to reload data or modify obtained data by using a different theory or with a different internal device structure every time the conditions including the curved shape of the object change, for example. For this reason, the method of visualizing information on the interior of an object using the inverse problem is difficult to use in a versatile manner; however, the scattering tomography is a versatile method. The image reconstructor 40 corresponds to the image reconstructor according to the present invention.

The image display 50 is a screen of a monitor and outputs, as video, data resulting from the arithmetic processing by the image reconstructor 40.

Figure 9:
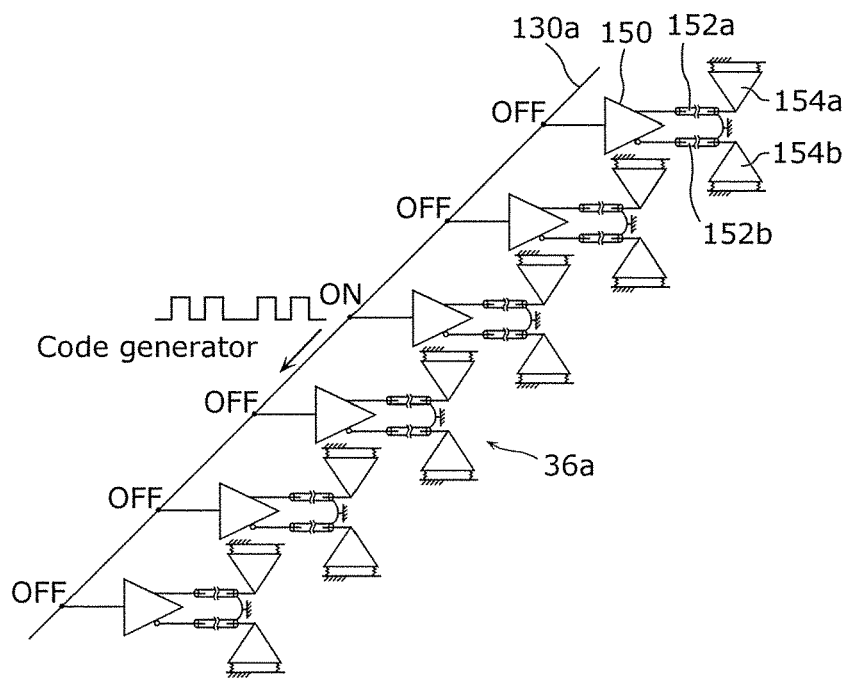
FIG. 9 schematically illustrates a configuration of a transmitting array antenna according to Embodiment 3.

FIG. 9 schematically illustrates the configuration of the transmitting array antenna.

As illustrated in FIG. 9, the transmitting array antenna includes the plurality of transmitting antenna elements 36a arranged in a straight line. Each of the transmitting antenna elements 36a includes a differential amplifier 150, coaxial cables 152a and 152b, antenna elements 154a and 154b, and a resistor 156 (refer to FIG. 11). The coaxial cable 130a is connected in common to the input terminals, each of which is one of the input terminals of a corresponding one of the differential amplifiers 150, of the differential amplifiers 150 in the transmitting antenna elements 36a.

With this, the codes generated by the code generator 31a are transmitted in sequence to the transmitting antenna elements 36a through the coaxial cable 130a. Therefore, the transmitting antenna elements 36a transmit signals in sequence from the antenna elements 154a and 154b.

Figure 10:
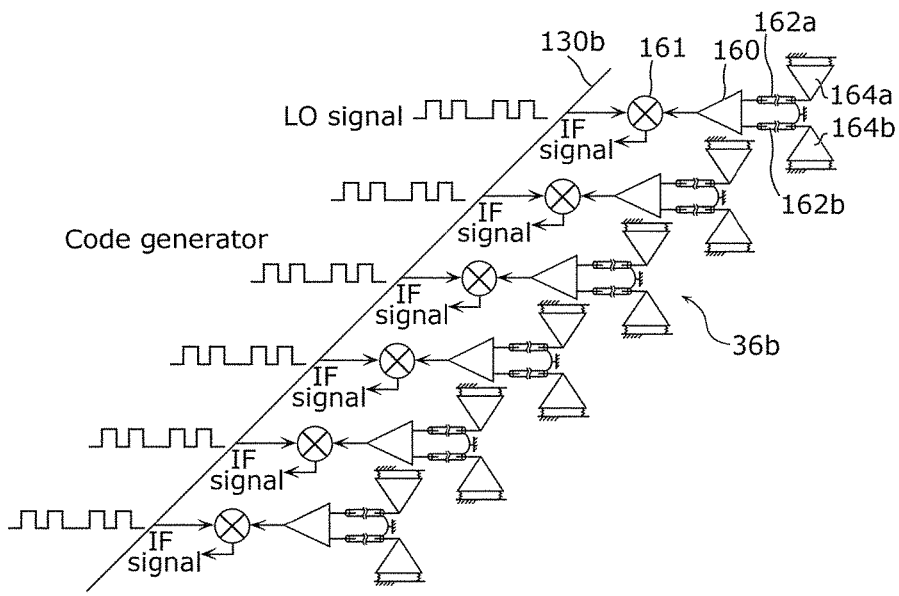
FIG. 10 schematically illustrates a configuration of a receiving array antenna according to Embodiment 3.

FIG. 10 schematically illustrates the configuration of the receiving array antenna.

As illustrated in FIG. 10, the receiving array antenna includes the plurality of receiving antenna elements 36b arranged in a straight line. Each of the receiving antenna elements 36b includes a differential amplifier 160, a mixer 161, coaxial cables 162a and 162b, antenna elements 164a and 164b, and a resistor 166 (refer to FIG. 13). The coaxial cable 130b is connected in common to the output terminals of the differential amplifiers 160 via the mixers 161 in the receiving antenna elements 36b.

With this, the signals received by the antenna elements 164a and 164b are transmitted in sequence to the receiving circuit 32a through the coaxial cable 130b. In this way, the receiving antenna elements 36b allow the receiving circuit 32a to detect the signals in sequence Next, the configuration of the transmitting antenna element 36a is described in more detail.

Figure 11:
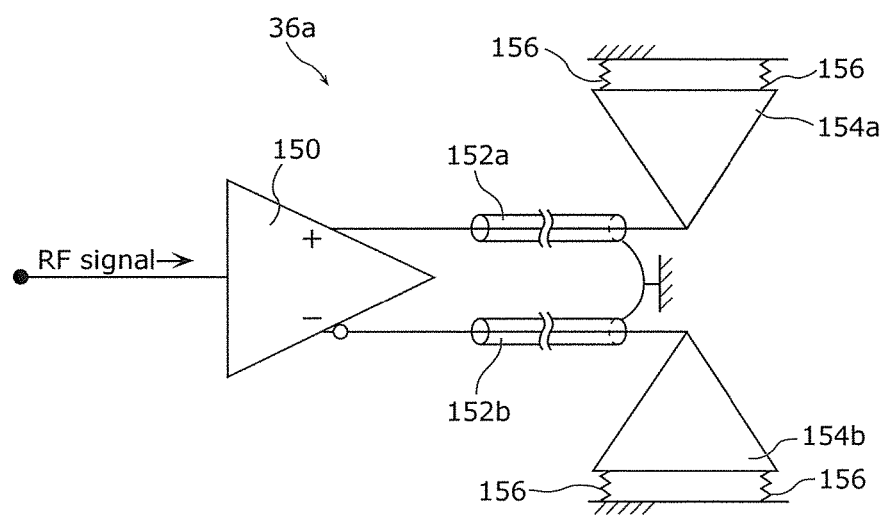
FIG. 11 schematically illustrates a configuration of a transmitting antenna element according to Embodiment 3.

FIG. 11 schematically illustrates the configuration of the transmitting antenna element 36a.

As illustrated in FIG. 11, the transmitting antenna element 36a includes the differential amplifier 150, the coaxial cables 152a and 152b, the antenna elements 154a and 154b, and the resistor 156 (refer to FIG. 11) as stated above.

The differential amplifier 150 is a complete differential amplifier including a plurality of semiconductor elements, for example, a plurality of transistors. The complete differential amplifier is an amplifier that has two input terminals and two output terminals, i.e., four terminals in total, and therefore operates in a differential mode at both the input and output terminals. One of the input terminals of the differential amplifier 150 in the transmitting antenna element 36a is connected to the coaxial cable 130a. The other input terminal of the differential amplifier 150 is grounded.

One of the output terminals of the differential amplifier 150 is connected to an internal conductor (a core) of the coaxial cable 152a, and the other output terminal is connected to an internal conductor (a core) of the coaxial cable 152b. The internal conductor of the coaxial cable 152a is connected to the antenna element 154a, and the internal conductor of the coaxial cable 152b is connected to the antenna element 154b. Outer conductors of both the coaxial cables 152a and 152b are grounded.

The antenna elements 154a and 154b constitute a bow-tie antenna, for example. A resistor 156 is provided to each of the antenna elements 154a and 154b. The resistor 156 is a termination resistor of each of the antenna elements 154a and 154b. One end of the resistor 156 is connected to each of the antenna elements 154a and 154b, and the other end of the resistor 156 is grounded.

In this transmitting antenna element 36a, suppose that a wave signal is input to the differential amplifier 150 through an unbalanced transmission line, such as the coaxial cable 130a. This signal is input to one input terminal of the differential amplifier 150 which is a complete differential amplifier. The other input terminal of the differential amplifier 150 is grounded. At this time, 180-degree-phase-shifted signals are amplified and output from two output terminals of this differential amplifier 150. The signals output from the differential amplifier 150 are output from the antenna elements 154a and 154b through the coaxial cables 152a and 152b.

The differential amplifier 150 corresponds to the first active balanced circuit in this embodiment. The antenna element 154a and the antenna element 154b correspond to the first antenna element and the second antenna element in this embodiment, respectively. The resistor 156 corresponds to the first resistance element according to the present invention. The transmitting antenna element 36a corresponds to the first wideband antenna according to the present invention.

The coaxial cables 152a and 152b are not always necessary and may be replaced by other types of cables. In this case, other types of cables may be directly connected to antenna elements 154a and 154b.

The following describes the configuration for using, as the transmitting antenna for UWB, the transmitting antenna element 36a described above. In order to use the transmitting antenna element 36a as the transmitting antenna for UWB, for example, the termination resistor, radio wave absorber, conductor cover, etc., of the antenna element need to have configurations suitable for UWB. Therefore, the following describes a practical configuration of the transmitting antenna for UWB.

Figure 12:
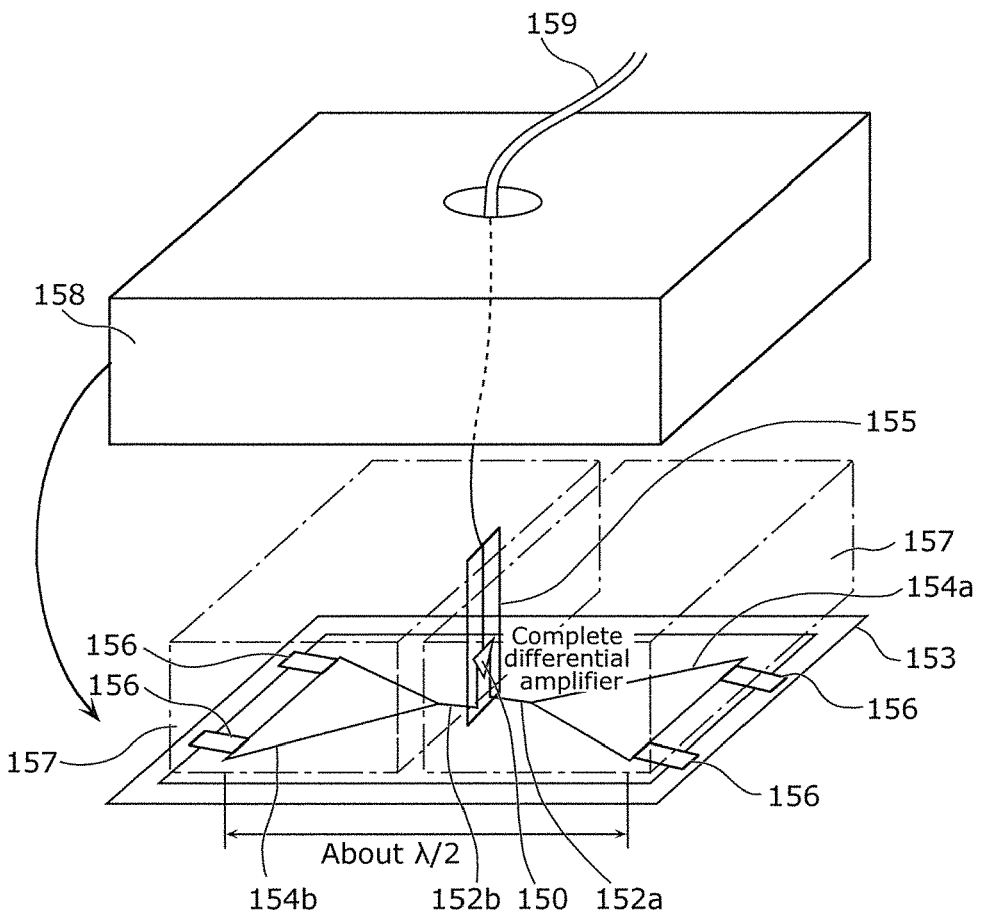
FIG. 12 schematically illustrates a configuration of a transmitting ultrawideband (UWB) antenna according to Embodiment 3.

FIG. 12 schematically illustrates the configuration of the transmitting UWB antenna.

As illustrated in FIG. 12, the antenna elements 154a and 154b and the resistor 156 illustrated in FIG. 11 are formed on a substrate 153 to form the transmitting UWB antenna.

The antenna elements 154a and 154b are formed in such a way that the input terminals thereof face each other. The distance between the output-terminal-side end of the antenna element 154a and the output-terminal-side end of the antenna element 154b is approximately half the wavelength.

The resistor 156 is connected to an earth terminal of the substrate 153. The resistor 156, which is the termination resistor of each of the antenna elements 154a and 154b, has a resistance value of 100Ω to 200Ω, for example.

Furthermore, on the substrate 153 on which the antenna elements 154a and 154b have been formed, radio wave absorbers 157 are provided so as to cover the respective antenna elements 154a and 154b. The radio wave absorbers 157 are made of ferrite, for example.

Furthermore, a substrate 155 is provided perpendicularly to the substrate 153, between the radio wave absorber 157 covering the antenna element 154a and the radio wave absorber 157 covering the antenna element 154b. The differential amplifier 150 is formed on the substrate 155.

Two output terminals of the differential amplifier 150 are connected to the input terminal of the antenna element 154a and the input terminal of the antenna element 154b. The input terminal of the differential amplifier 150 is connected to a coaxial cable 159.

Furthermore, a metal case 158 is provided so as to cover the substrate 153 and the antenna elements 154a and 154b, the substrate 155, the differential amplifier 150, and the radio wave absorbers 157 formed on the substrate 153. The metal case 158 is connected to the substrate 153 and the substrate 155 and thus is grounded. With this configuration, it is possible to provide the transmitting antenna for UWB while reducing influence of noise from outside.

Next, the receiving antenna element 36b is described in more detail.

Figure 13:
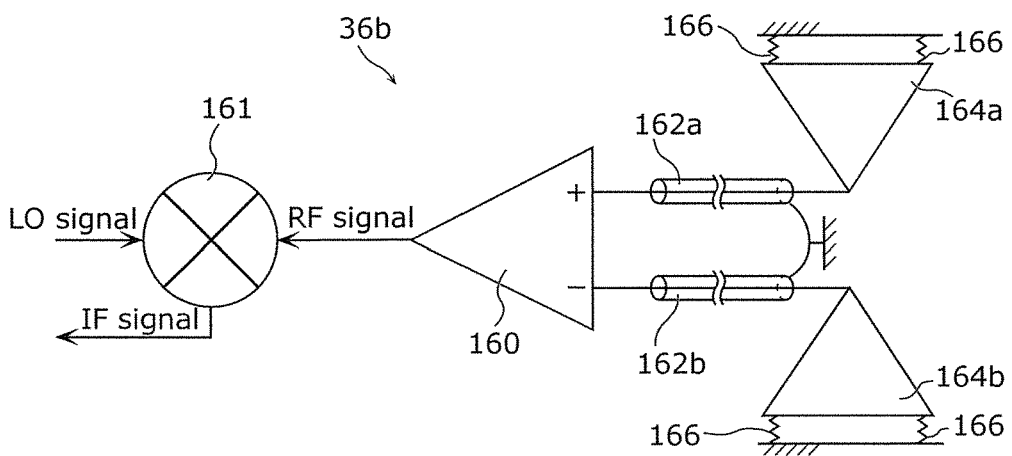
FIG. 13 schematically illustrates a configuration of a receiving antenna element according to Embodiment 3.

FIG. 13 schematically illustrates the configuration of the receiving antenna element 36b.

As illustrated in FIG. 13, the receiving antenna element 36b includes the differential amplifier 160, the mixer 161, the coaxial cables 162a and 162b, the antenna elements 164a and 164b, and the resistor 166 (refer to FIG. 13).

The differential amplifier 160 is a differential amplifier including a plurality of semiconductor elements. The differential amplifier 160 has two input terminals and one output terminal. In the receiving antenna element 36b, the output terminal of the differential amplifier 160 is connected to the coaxial cable 130b via the mixer 161.

One of the input terminals of the differential amplifier 160 is connected to an internal conductor (a core) of the coaxial cable 162a, and the other input terminal is connected to an internal conductor (a core) of the coaxial cable 162b. The internal conductor of the coaxial cable 162a is connected to the antenna element 164a, and the internal conductor of the coaxial cable 162b is connected to the antenna element 164b.

Outer conductors of both the coaxial cables 162a and 162b are grounded. One end of the resistor 166 is connected to each of the antenna elements 164a and 164b. The other end of the resistor 166 is grounded.

With this configuration, the signals received by the antenna elements 164a and 164b are input to the input terminals of the differential amplifier 160 through the coaxial cables 162a and 162b. The signals received by the antenna elements 164a and 164b (the RF signals) are a digital code sequence, and detected in the N channels simultaneously or guided by an external switch to one wave-detecting circuit and detected therein.

The mixer 161 is connected to the output terminal of the differential amplifier 160. The mixer 161 outputs intermediate frequency band (IF) signals as a result of converting the frequency of signals into the IF by mixing the output from the differential amplifier 160 with reference local signals (LO signals) at the transmission frequency. In short, the mixer 161 converts the frequency of received frequency signals and outputs the resultant signals. In the mixer 161, the same code as a transmission code is delayed, and a wave-detection code with the number of delayed bits controlled is used as the LO signals for the mixer 161. The signals output from the mixer 161 (the detected signals) are input to an A/D converter (not illustrated in the Drawings) of the control device 136 as the IF signals through an IF filter and an IF amplifier (not illustrated in the Drawings), and then are recorded in a memory (not illustrated in the Drawings).

The differential amplifier 160 corresponds to the second active balanced circuit in this embodiment. The antenna element 164a and the antenna element 164b correspond to the third antenna element and the fourth antenna element in this embodiment, respectively. The resistor 166 corresponds to the second resistance element according to the present invention. The receiving antenna element 36b corresponds to the second wideband antenna according to the present invention.

The foregoing describes the process of correlating the signals received by the receiving antenna element 36b with the signals transmitted from the transmitting antenna element 36a. The final process of the correlation is performed by a calculator (not illustrated in the Drawings), and mathematically the same result as a pulse response is obtained.

Note that complete differential amplifiers having the same configuration may be used as the differential amplifier 150 and the differential amplifier 160. In this case, as the differential amplifier 150 for use in the transmitting antenna element 36a, one of two input terminals of the complete differential amplifier may be used as the input terminal, and the other input terminal may be grounded. As the differential amplifier 160 for use in the receiving antenna element 36b, one of two output terminals of the complete differential amplifier may be used as the output terminal, and the other output terminal may be terminated.

The following describes the configuration for using, as the receiving antenna for UWB, the receiving antenna element 36b described above.

Figure 14:
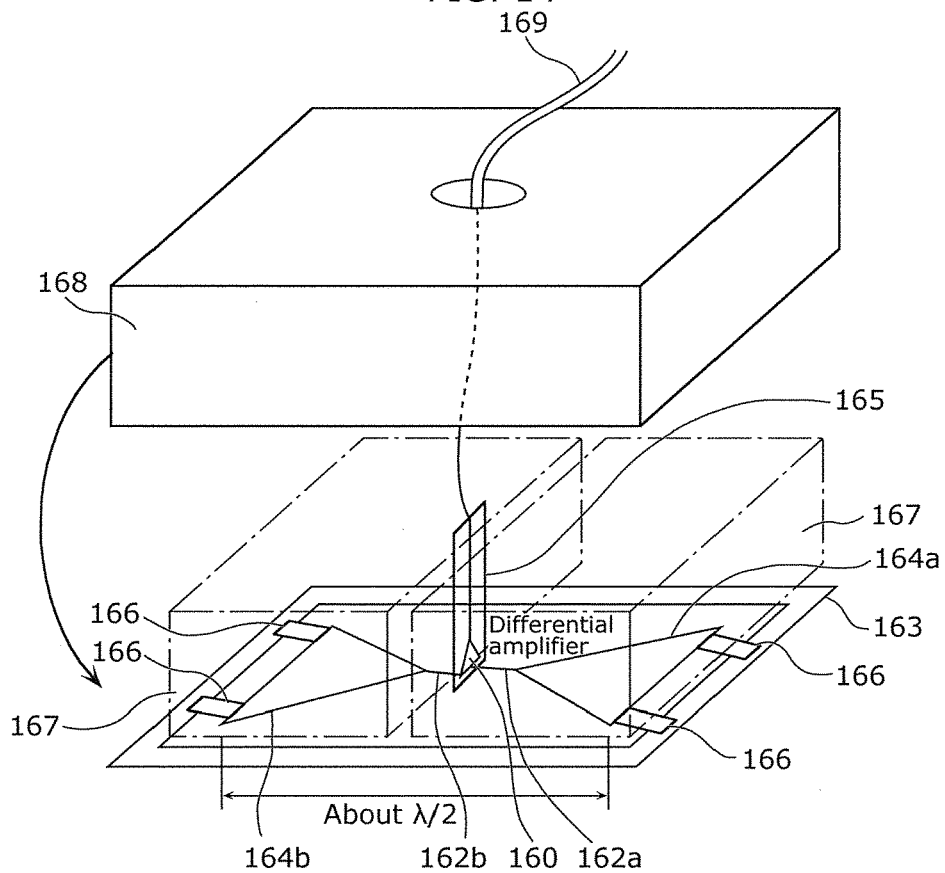
FIG. 14 schematically illustrates a configuration of a receiving UWB antenna according to Embodiment 3.

FIG. 14 schematically illustrates the configuration of the receiving UWB antenna.

The configuration of the receiving UWB antenna is substantially the same as the configuration of the transmitting UWB antenna described above. As illustrated in FIG. 14, the antenna elements 164a and 164b and the resistor 166 illustrated in FIG. 13 are formed on the substrate 163 to form the receiving UWB antenna.

The antenna elements 164a and 164b are formed in such a way that the output terminals thereof face each other. The distance between the input-terminal-side end of the antenna element 164a and the input-terminal-side end of the antenna element 164b is approximately half the wavelength.

The resistor 166 is connected to an earth terminal of the substrate 163. The resistor 166, which is the termination resistor of each of the antenna elements 164a and 164b, has a resistance value of $100\Omega$ to $200\Omega$, for example.

Furthermore, on the substrate 163 on which the antenna elements 164a and 164b have been formed, radio wave absorbers 167 are provided so as to cover the respective antenna elements 164a and 164b. The radio wave absorbers 167 are made of ferrite, for example.

Furthermore, a substrate 165 is provided perpendicularly to the substrate 163, between the radio wave absorber 167 covering the antenna element 164a and the radio wave absorber 167 covering the antenna element 164b. The differential amplifier 160 is formed on the substrate 165.

Two input terminals of the differential amplifier 160 are connected to the output terminal of the antenna element 164a and the output terminal of the antenna element 164b. The output terminal of the differential amplifier 160 is connected to a coaxial cable 169. Furthermore, the mixer 161 (not illustrated in the Drawings) is connected to the coaxial cable 169.

Furthermore, a metal case 168 is provided so as to cover the substrate 163 and the antenna elements 164a and 164b, the substrate 165, the differential amplifier 160, and the radio wave absorbers 167 formed on the substrate 163. The metal case 168 is connected to the substrate 163 and the substrate 165 and thus is grounded. With this configuration, it is possible to provide the receiving antenna for UWB while reducing influence of noise from outside.

The following briefly describes an analysis model in the image reconstructor 40 that is applied in the case where the antenna system 100 described above is used as mammography equipment.

Figure 15:
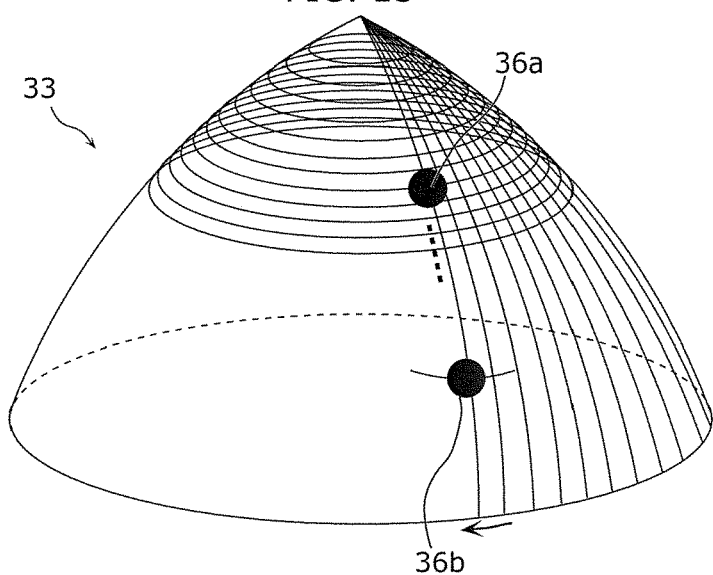
FIG. 15 illustrates an analysis model for a surface of an examination subject according to Embodiment 3.

FIG. 15 illustrates an analysis model for a surface of the case 33 according to this embodiment.

As described above, the case 33 has a substantially conical shape, and the array antenna 37 according to this embodiment is provided along the generatrix of the substantially conical shape of the case 33. The size of the transmitting antenna element 36a and the receiving antenna element 36b included in the array antenna 37 is, for example, approximately 5 mm to 10 mm.

At the examination, microwaves are transmitted from the transmitting antenna element 36a to the examination subject placed in the case 33. The frequency of the microwaves is 0.4 GHz to 12.0 GHz, for example. The microwaves reflected in the examination subject placed in the case 33 are then received by the receiving antenna element 36b. If the examination subject placed in the case 33 has a flaw (for example, a cancer cell), the received signals represent such data. All the transmitting antenna elements 36a and the receiving antenna elements 36b sequentially perform this operation. Furthermore, the array antenna 37 is rotated through a predetermined angle, and the examination is conducted likewise so that stereoscopic information on the position of a flaw inside the examination subject placed in the case 33 can be obtained.

The spatial resolution of mammography is approximately 1.97 mm when the size of the transmitting antenna element 36a and the receiving antenna element 36b is approximately 5 mm to 10 mm and the frequency of the microwaves is 10 GHz. Therefore, it is possible to conduct high-speed, high-resolution examination by using the antenna system according to this embodiment as mammography equipment.

Thus, with the antenna system 100 described above, a balun configured of a coil transducer is not used in a ultrawideband antenna, and therefore the frequency band of signals to be transmitted and received is not limited by the number of turns and the size of the coil. Furthermore, the complete differential amplifier including semiconductor elements and having two input terminals and two output terminals is used as a substitute for the balun, and thus signals can be transmitted and received at high speed. Therefore, it is possible to provide an ultrawideband antenna that operates at high speed and supports a frequency band not limited by the number of turns and the size of a coil. The ultrawideband antenna according to this embodiment is capable of supporting a direct current even to a superhigh frequency of 10 GHz or more, for example. This makes it possible to provide high-speed, accurate mammography equipment.

Note that the differential amplifier 150 used in the transmitting antenna element 36a according to this embodiment is not limited to being used in the above-described antenna system and mammography, and may be used in the FPGA included in the code generator 31a illustrated in FIG. 8, for example.

Specifically, the complete differential amplifier used as the differential amplifier 150 is attached to the output terminal of the FPGA, allowing the FPGA to output a pair of 180-degree-phase-shifted signals.

For example, in order to provide a digital code generator capable of generating signals at the maximum frequency of 12 GHz in a region of the spectrum using the FPGA that runs at an operation clock of 1 GHz or less, a code is generated as 10-bit parallel signals and converted from parallel to series, resulting in 10 gigabit-per-second (Gbps) signals which are 10 times higher in speed than the original signals. At this time, the complete differential amplifier is attached to the output terminal so that the code can be read in parallel from the memory of the FPGA to ultimately generate serial high-speed signals. Thus, the differential amplifier 150 according to this embodiment can be used not only in the transmitting antenna element 36a, but also as an element of a high-speed code generator.

[Variation]

Next, a variation of the embodiments according to the present invention is described with reference to FIG. 16A and FIG. 16B.

Figure 16A:
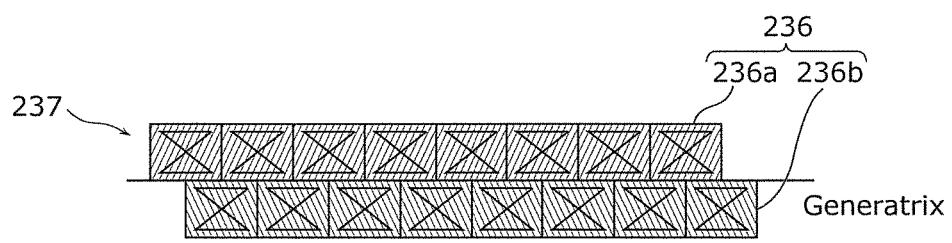
FIG. 16A schematically illustrates an example of a configuration of an antenna element.

The arrangement of antenna elements in the array antenna according to the present embodiment is not limited to the above-described arrangement, and may be an arrangement such as that illustrated in FIG. 16A. Specifically, as illustrated in FIG. 16A, in an array antenna 237, transmitting antennas 236a and receiving antennas 236b that constitute antenna elements 236 may be aligned on opposite sides of the generatrix in such a way that transmitting antennas 236a and receiving antennas 236b are shifted by half an antenna from each other.

Figure 16B:
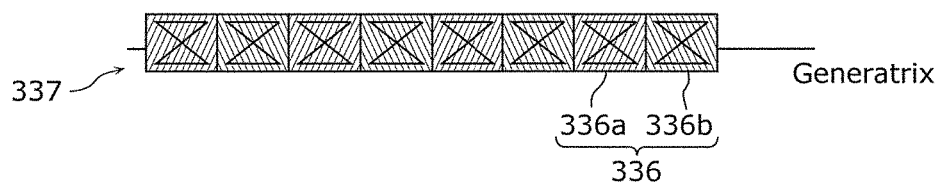
FIG. 16B schematically illustrates another example of a configuration of an antenna element.

Furthermore, the array antenna may be configured as illustrated in FIG. 16B. Specifically, as illustrated in FIG. 16B, in an array antenna 337, transmitting antennas 336a and receiving antennas 336b that constitute antenna elements 336 may be alternately aligned on one generatrix.

The arrangements of the transmitting antennas and the receiving antennas are not limited to these arrangements and may be any arrangement in which the array antennas each including the transmitting antenna and the receiving antenna are formed in one line.

Note that the above mathematical expressions and process flow of deriving the mathematical expressions are one example; other mathematical expressions and other deriving process flow may be used.

Although the microwaves are used as the waves in the foregoing embodiments, the waves are not limited to the microwaves and may be electromagnetic waves or ultrasonic waves in other frequency bands or may be wideband or ultrawideband electromagnetic waves or ultrasonic waves. Furthermore, although periodic waves having a predetermined frequency are used in the embodiments because the microwaves are used, the waves may be pulsed waves or the like instead of the periodic waves.

Furthermore, although a living body, specifically, a breast, is cited as an example of a target in the foregoing embodiments, the object is not limited to a breast and may be other living structures or object structures different from living structures. For example, a structure such as a conical concrete post is applicable.

Hereinbefore, the scattering tomography method, the scattering tomography device, and the array antenna system included in the scattering tomography device according to the present invention have been described based on the embodiments, but the present invention is not limited to these embodiments. The scope of the present invention may also include embodiments as a result of adding various modifications to the embodiments that may be conceived by those skilled in the art, and other embodiments obtained by combining structural elements in the embodiments in any manner.

For example, in the scattering tomography device, a process which a specific processing unit performs may be performed by another processing unit. For example, only the array antenna system included in the scattering tomography device may be operated by another processing unit. Furthermore, in the scattering tomography method, the process sequence may be changed, and a plurality of processes may be performed in parallel.

Furthermore, although the transmitting antenna elements and the receiving antenna elements are alternately arranged in a straight line in the array antenna system described in the foregoing embodiments, the transmitting antenna elements and the receiving antenna elements are not limited to being alternately arranged in a straight line; a transmitting array antenna in which only the transmitting antenna elements are arranged in a straight line and a receiving array antenna in which only the receiving antenna elements are arranged in a straight line may be arranged in parallel.

A step in the scattering tomography method according to the present invention may be performed by a computer. Furthermore, the present invention may be provided as a program for causing a computer to perform a step included in the scattering tomography method. Moreover, the present invention may be provided as a non-transitory, computer-readable recording medium such as a compact disc read-only memory (CD-ROM) on which the program has been recorded.

A plurality of structural elements included in the scattering tomography device may be provided as large scale integration (LSI), which is an integrated circuit. These structural elements may be individually configured as single chips or may be configured so that a part or all of the structural elements are included in a single chip. The name used here is LSI, but it may also be called an integrated circuit (IC), system LSI, super LSI, or ultra LSI depending on the degree of integration.

Moreover, ways to achieve integration are not limited to the LSI, and a dedicated circuit or a general-purpose processor can also achieve the integration. A field programmable gate array (FPGA) which allows programming or a reconfigurable processor which allows reconfiguration of the connections and settings of the circuit cells inside the LSI may also be used.

Furthermore, when advancement in semiconductor technology or derivatives of other technologies brings forth a circuit integration technology which replaces LSI, it will be appreciated that such a circuit integration technology may be used to integrate the structural elements included in the scattering tomography device.

Although only some exemplary embodiments of the present invention have been described in detail above, those skilled in the art will readily appreciate that many modifications are possible in the exemplary embodiments without materially departing from the novel teachings and advantages of the present invention. Accordingly, all such modifications are intended to be included within the scope of the present invention.

INDUSTRIAL APPLICABILITY

A scattering tomography method and a scattering tomography device according to the present invention are useful for inspection of an object with high curvature and are applicable to, for example, medical devices, inspection of reinforcing steel inside concrete for corrosion, and inspection of reinforcing steel structures for seismic resistance in a disaster area.

The invention claimed is:

1. A scattering tomography method for analyzing scattered waves of waves radiated to an object placed in a case, the scattering tomography method comprising:
  radiating the waves to the object from a plurality of transmitting antenna elements aligned on a side surface of the case in a same direction as an axis of rotational symmetry of the case when seen in a plan view;
  receiving the scattered waves by a plurality of receiving antenna elements aligned on the side surface of the case in the same direction as the axis of rotational symmetry of the case when seen in a plan view; and
  reconstructing an image relating to information on an interior of the object using scattered wave data representing the scattered waves received by the plurality of receiving antenna elements,
  wherein in the reconstructing:
  a reconstruction function for reconstructing the image relating to the information on the interior of the object is set in advance for a three-dimensional space having a same shape as the case;
  a scattering field equation whose solution is the reconstruction function is constructed, the scattering field equation being a linear partial differential equation whose solution is a scattering field in which the scattered waves are present at each point in a space that (i) is defined by independent variables representing positions of, among the plurality of transmitting antenna elements and the plurality of receiving antenna elements, a transmitting antenna element and a receiving antenna element that correspond to two arbitrary points inside the object, and (ii) has as many dimensions as a total number of the independent variables representing the positions of the transmitting antenna element and the receiving antenna element;

a visualization function is derived from the scattered wave data, the visualization function (i) being limits of a time variable and a space variable of a function obtained by solving the linear partial differential equation and (ii) involving an angle θ of rotation of a tangent plane about the axis of rotational symmetry of the case, the tangent plane being a plane tangent to the case at the positions of the transmitting antenna element and the receiving antenna element; and the image relating to the information on the interior of the object is reconstructed using a function obtained by integrating the visualization function with respect to the angle θ.

2. The scattering tomography method according to claim 1, wherein the visualization function is represented by Expression C, and the function obtained by integrating the visualization function with respect to the angle θ is represented by Expression D,

[Math. 1]

$$\rho(x, y, z, \theta) = \int_{-\infty}^{\infty} \phi(x, y, y, z, z, k)dk$$

$$= \int_{-\infty}^{\infty} \lim_{y_1 \to y} \left[ \frac{1}{(2\pi)^3} \int_{-\infty}^{\infty} \int_{-\infty}^{\infty} \int_{-\infty}^{\infty} e^{-i(k_x x + k_{y_1} y_1 + k_{y_2} y)} a_\theta(k_x, k_{y_1}, k_{y_2}, k) e^{i[s_1(k)+s_2(k)]z} dk_x dk_{y_1} dk_{y_2} \right] dk$$

$$= \int_{-\infty}^{\infty} \lim_{y_1 \to y} \left[ \frac{1}{(2\pi)^3} \int_{-\infty}^{\infty} \int_{-\infty}^{\infty} \int_{-\infty}^{\infty} e^{-i(k_x x + k_{y_1} y_1 + k_{y_2} y)} a_\theta(k_x, k_{y_1}, k_{y_2}, k) e^{iz\left\{\left(\sqrt{k^2-k_{y_1}^2} + \sqrt{k^2-k_{y_2}^2}\right)^2 k_x^2\right\}} dk_x dk_{y_1} dk_{y_2} \right] dk$$

$$= \lim_{y_1 \to y} \left[ \frac{1}{(2\pi)^3} \int_{-\infty}^{\infty} \int_{-\infty}^{\infty} \int_{-\infty}^{\infty} \int_{-\infty}^{\infty} e^{-i(k_x x + k_{y_1} y_1 + k_{y_2} y - k_z z)} a_\theta(k_x, k_{y_1}, k_{y_2}, k) \left(\frac{dk}{dk_z}\right) dk_x dk_{y_1} dk_{y_2} dk_z \right]$$

Expression C

[Math. 2]

$$P(X, Y, Z) = \int_0^{2\pi} \rho(x, y, z, \theta)d\theta$$

Expression D where x is an x-coordinate of a position of the transmitting antenna element and a position of the receiving antenna element, $y_1$ is a y-coordinate of the position of the transmitting antenna element, $y_2$ is a y-coordinate of the position of the receiving antenna element, z is a z-coordinate of the position of the transmitting antenna element and the position of the receiving antenna element, Z is a coordinate along the axis of rotational symmetry of the case, X is a coordinate in one arbitrary direction in a plane perpendicular to the axis of rotational symmetry of the case, Y is a coordinate in a direction perpendicular to a direction of the X in the plane perpendicular to the axis of rotational symmetry of the case, p is a function of permittivity, φ is the reconstruction function, $a_\theta$, $s_1$, and $s_2$ are coefficients, and $k_x$, $k_{y_1}$, $k_{y_2}$, and $k_z$ are an x component of a wave number, a $y_1$ component of the wave number, a $y_2$ component of the wave number, and a z component of the wave number, respectively.

3. The scattering tomography method according to claim 2, wherein the case is in the shape of a substantial cone having a curved generatrix, and the plurality of transmitting antenna elements and the plurality of receiving antenna elements are arranged along the curved generatrix.

4. The scattering tomography method according to claim 1, wherein the waves are microwaves.

5. The scattering tomography method according to claim 1, wherein the waves are pulsed waves or periodic waves having a predetermined frequency.

6. The scattering tomography method according to claim 1, wherein the visualization function is represented by Expression A, and the function obtained by integrating the visualization function with respect to the angle θ is represented by Expression B,

[Math. 5]

Expression A $$\rho(x, y, z, \theta) = \int_{-\infty}^{\infty} \phi(x, y, y, z, k) dk$$

$$= \int_{-\infty}^{\infty} \lim_{y_1 \to y} [\phi(x, y_1, y, z, k)] dk$$

$$= \int_{-\infty}^{\infty} \lim_{y_1 \to y} \left[ \frac{1}{(2\pi)^3} \int_{-\infty}^{\infty} \int_{-\infty}^{\infty} \int_{-\infty}^{\infty} e^{-i(k_x x + k_{y1} y_1 + k_{y2} y)} a_\theta(k_x, k_{y_1}, k_{y_2}, k) e^{i \left\{ \sqrt{\left( \sqrt{k^2 - k_{y_1}^2} + \sqrt{k^2 - k_{y_2}^2} \right)^2 k_x^2} \right\}} dk_x dk_{y_1} dk_{y_2} \right] dk$$

$$= \int_{-\infty}^{\infty} \lim_{y_1 \to y} \left[ \frac{1}{(2\pi)^3} \int_{-\infty}^{\infty} \int_{-\infty}^{\infty} \int_{-\infty}^{\infty} e^{-i(k_x x + k_{y1} y_1 + k_{y2} y)} e^{i k_z z} \tilde{\phi}_R(k_{y_1}, k_{y_2}, k, \theta) \left( \frac{dk}{dk_z} \right) dk_x dk_{y_1} dk_{y_2} dk_z \right]$$

[Math. 6]

Expression B $$P(X, Y, Z) = \int_0^{2\pi} \rho(x, y, z, \theta) d\theta$$

where x is an x-coordinate of a position of the transmitting antenna element and a position of the receiving antenna element, $y_1$ is a y-coordinate of the position of the transmitting antenna element, $y_2$ is a y-coordinate of the position of the receiving antenna element, z is a z-coordinate of the position of the transmitting antenna element and the position of the receiving antenna element, Z is a coordinate along the axis of rotational symmetry of the case, X is a coordinate in one arbitrary direction in a plane perpendicular to the axis of rotational symmetry of the case, Y is a coordinate in a direction perpendicular to a direction of the X in the plane perpendicular to the axis of rotational symmetry of the case, ρ is a function of permittivity, φ is the reconstruction function, a is a coefficient, and $k_x$, $k_{y1}$, $k_{y2}$, and $k_z$ are an x component of a wave number, a $y_1$ component of the wave number, a $y_2$ component of the wave number, and a z component of the wave number, respectively.

7. The scattering tomography method according to claim 6,
wherein the case is in the shape of a cone, and
the plurality of transmitting antenna elements and the plurality of receiving antenna elements are arranged along a generatrix of the cone of the case.

8. A scattering tomography device for analyzing scattered waves of waves radiated to an object placed in a case, the scattering tomography device comprising:
a plurality of transmitting antenna elements that are aligned on a side surface of the case in a same direction as an axis of rotational symmetry of the case when seen in a plan view, and radiate the waves to the object;
a plurality of receiving antenna elements that are aligned on the side surface of the case in the same direction as the axis of rotational symmetry of the case when seen in a plan view, and receive the scattered waves that are the waves radiated to the object and scattered in the object; and
an image reconstructor that reconstructs an image relating to information on an interior of the object using scattered wave data representing the scattered waves received by the plurality of receiving antenna elements,
wherein the image reconstructor:
sets in advance a reconstruction function for reconstructing the image relating to the information on the interior of the object, for a three-dimensional space having a same shape as the case;
constructs a scattering field equation whose solution is the reconstruction function and that is a linear partial differential equation whose solution is a scattering field in which the scattered waves are present at each point in a space that (i) is defined by independent variables representing positions of, among the plurality of transmitting antenna elements and the plurality of receiving antenna elements, a transmitting antenna element and a receiving antenna element that correspond to two arbitrary points inside the object, and (ii) has as many dimensions as a total number of the independent variables representing the positions of the transmitting antenna element and the receiving antenna element;
derives a visualization function from the scattered wave data, the visualization function (i) being limits of a time variable and a space variable of a function obtained by solving the linear partial differential equation and (ii) involving an angle θ of rotation of a tangent plane about the axis of rotational symmetry of the case, the tangent plane being a plane tangent to the case at the positions of the transmitting antenna element and the receiving antenna element; and
reconstructs, using a function obtained by integrating the visualization function with respect to the angle θ, the image relating to the information on the interior of the object.

9. The scattering tomography device according to claim 8,
wherein the visualization function is represented by Expression C, and
the function obtained by integrating the visualization function with respect to the angle θ is represented by Expression D,

[Math. 3]

Expression C $$\rho(x, y, z, \theta) = \int_{-\infty}^{\infty} \phi(x, y, y, z, z, k) dk$$

$$= \int_{-\infty}^{\infty} \lim_{y_1 \to y} \left[ \frac{1}{(2\pi)^3} \int_{-\infty}^{\infty} \int_{-\infty}^{\infty} \int_{-\infty}^{\infty} e^{-i(k_x x + k_{y1} y_1 + k_{y2} y)} a_\theta(k_x, k_{y_1}, k_{y_2}, k) e^{i[s_1(k) + s_2(k)]z} dk_x dk_{y_1} dk_{y_2} \right] dk$$

$$= \int_{-\infty}^{\infty} \lim_{y_1 \to y} \left[ \frac{1}{(2\pi)^3} \int_{-\infty}^{\infty} \int_{-\infty}^{\infty} \int_{-\infty}^{\infty} e^{-i(k_x x + k_{y1} y_1 + k_{y2} y)} a_\theta(k_x, k_{y_1}, k_{y_2}, k) e^{iz\left\{\sqrt{\left(\sqrt{k^2 - k_{y_1}^2} + \sqrt{k^2 - k_{y_2}^2}\right)^2 k_x^2}\right\}} dk_x dk_{y_1} dk_{y_2} \right] dk$$

$$= \lim_{y_1 \to y} \left[ \frac{1}{(2\pi)^3} \int_{-\infty}^{\infty} \int_{-\infty}^{\infty} \int_{-\infty}^{\infty} \int_{-\infty}^{\infty} e^{-i(k_x x + k_{y1} y_1 + k_{y2} y - k_z z)} a_\theta(k_x, k_{y_1}, k_{y_2}, k) \left(\frac{dk}{dk_z}\right) dk_x dk_{y_1} dk_{y_2} dk_z \right]$$

[Math. 4]

Expression D $$P(X, Y, Z) = \int_0^{2\pi} \rho(x, y, z, \theta) d\theta$$

where x is an x-coordinate of a position of the transmitting antenna element and a position of the receiving antenna element, $y_1$ is a y-coordinate of the position of the transmitting antenna element, $y_2$ is a y-coordinate of the position of the receiving antenna element, z is a z-coordinate of the position of the transmitting antenna element and the position of the receiving antenna element, Z is a coordinate along the axis of rotational symmetry of the case, X is a coordinate in one arbitrary direction in a plane perpendicular to the axis of rotational symmetry of the case, Y is a coordinate in a direction perpendicular to a direction of the X in the plane perpendicular to the axis of rotational symmetry of the case, ρ is a function of permittivity, φ is the reconstruction function, $a_\theta$, $s_1$, and $s_2$ are coefficients, and $k_x$, $k_{y1}$, $k_{y2}$, and $k_z$ are an x component of a wave number, a $y_1$ component of the wave number, a $y_2$ component of the wave number, and a z component of the wave number, respectively.

10. The scattering tomography device according to claim 9,
wherein the case is in the shape of a substantial cone having a curved generatrix, and
the plurality of transmitting antenna elements and the plurality of receiving antenna elements are arranged along the curved generatrix.

11. The scattering tomography device according to claim 8,
wherein each of the plurality of transmitting antenna elements includes
a first wideband antenna including:
a first active balanced circuit that has two input terminals and two output terminals and includes a semiconductor element;
a first antenna element connected to one of the two output terminals;
a second antenna element connected to a remaining one of the two output terminals; and
a first resistance element that causes each of the first antenna element and the second antenna element to be grounded, and
each of the plurality of receiving antenna elements includes
(i) a second wideband antenna including:
a second active balanced circuit that has two input terminals and two output terminals and includes a semiconductor element;
a third antenna element connected to one of the two input terminals;
a fourth antenna element connected to a remaining one of the two input terminals; and
a second resistance element that causes each of the third antenna element and the fourth antenna element to be grounded, and
(ii) a mixer that converts a frequency of a received frequency signal.

12. The scattering tomography device according to claim 8,
wherein the waves are microwaves.

13. The scattering tomography device according to claim 8,
wherein the waves are pulsed waves or periodic waves having a predetermined frequency.

14. The scattering tomography device according to claim 8,
wherein the visualization function is represented by Expression A, and
the function obtained by integrating the visualization function with respect to the angle θ is represented by Expression B,

[Math. 7]

Expression A $$\rho(x, y, z, \theta) = \int_{-\infty}^{\infty} \phi(x, y, y, z, k) dk$$

$$= \int_{-\infty}^{\infty} \lim_{y_1 \to y}[\phi(x, y_1, y, z, k)] dk$$

$$= \int_{-\infty}^{\infty} \lim_{y_1 \to y}\left[\frac{1}{(2\pi)^3} \int_{-\infty}^{\infty}\int_{-\infty}^{\infty}\int_{-\infty}^{\infty} e^{-i(k_x x + k_{y1} y_1 + k_{y2} y)} a_\theta(k_x, k_{y_1}, k_{y_2}, k) e^{i\left\{\sqrt{\left(\sqrt{k^2-k_{y_1}^2}+\sqrt{k^2-k_{y_2}^2}\right)^2 k_x^2}\right\}} dk_x dk_{y_1} dk_{y_2}\right] dk$$

$$= \int_{-\infty}^{\infty} \lim_{y_1 \to y}\left[\frac{1}{(2\pi)^3} \int_{-\infty}^{\infty}\int_{-\infty}^{\infty}\int_{-\infty}^{\infty} e^{-i(k_x x + k_{y1} y_1 + k_{y2} y)} e^{ik_z z} \tilde{\phi}_R(k_{y_1}, k_{y_2}, k, \theta)\left(\frac{dk}{dk_z}\right) dk_x dk_{y_1} dk_{y_2} dk_z\right]$$

[Math. 8]

Expression B $$P(X, Y, Z) = \int_0^{2\pi} \rho(x, y, z, \theta) d\theta$$

where x is an x-coordinate of a position of the transmitting antenna element and a position of the receiving antenna element, $y_1$ is a y-coordinate of the position of the transmitting antenna element, $y_2$ is a y-coordinate of the position of the receiving antenna element, z is a z-coordinate of the position of the transmitting antenna element and the position of the receiving antenna element, Z is a coordinate along the axis of rotational symmetry of the case, X is a coordinate in one arbitrary direction in a plane perpendicular to the axis of rotational symmetry of the case, Y is a coordinate in a direction perpendicular to a direction of the X in the plane perpendicular to the axis of rotational symmetry of the case, ρ is a function of permittivity, φ is the reconstruction function, a is a coefficient, and $k_x$, $k_{y1}$, $k_{y2}$, and $k_z$ are an x component of a wave number, a $y_1$ component of the wave number, a $y_2$ component of the wave number, and a z component of the wave number, respectively.

15. The scattering tomography device according to claim 14,
wherein the case is in the shape of a cone, and
the plurality of transmitting antenna elements and the plurality of receiving antenna elements are arranged along a generatrix of the cone of the case.

* * * * *

UNITED STATES PATENT AND TRADEMARK OFFICE
CERTIFICATE OF CORRECTION

PATENT NO. : 10,101,282 B2
APPLICATION NO. : 15/262448
DATED : October 16, 2018
INVENTOR(S) : Kenjiro Kimura Page 1 of 2

It is certified that error appears in the above-identified patent and that said Letters Patent is hereby corrected as shown below:

In the Specification

Column 13, Line 47 (Expression 9), "$(y_2\eta)^2$" should be changed to -- $(y_2-\eta)^2$ --.

Column 15, Line 54 (Expression 19), "$\varphi_R$" should be changed to -- $\phi_R$ --.

Column 25, at the end of the equations on Lines 47 and 49 (Expression 41), insert -- $\phi$ --.

Column 25, at the end of the equation on Line 58 (Expression 42), insert -- $\phi$ --.

Column 27, Line 62 (Expression 54), "$k_{11}$" should be changed to -- $k_{y1}$ --.

Column 28, Line 60 (Expression 60), "zk" should be changed to -- z, k --.

Column 29, Line 6 (Expression 61), "ikt" should be changed to -- -ikt --.

Column 29, Line 28 (Expression 64), "ikt" should be changed to -- -ikt --.

Column 29, Line 42 (Expression 65), "$\phi_{RE}$" should be changed to -- $\phi_R$ --.

Column 29, Line 62 (Expression 67), "i(" should be changed to -- -i( --.

Column 30, Line 19 (Expression 68), "δx" should be changed to -- dx --.

Column 31, Line 42 (Expression 75), "zk" should be changed to -- z, k --.

Column 31, Line 44 (Expression 75), "y2" should be changed to -- y --.

Column 31, Line 46 (Expression 75), "y2" should be changed to -- y --.

Signed and Sealed this
Twenty-third Day of April, 2019

Andrei Iancu
*Director of the United States Patent and Trademark Office*

CERTIFICATE OF CORRECTION (continued)
U.S. Pat. No. 10,101,282 B2

Column 31, Line 48 (Expression 75), "y2" should be changed to -- $y-k_z z$ --.

Column 33, Line 45 (Expression 84), "α0" should be changed to -- $\alpha\theta$ --.

Column 33, Line 47 (Expression 84), "α0" should be changed to -- $\alpha\theta$ --.

Column 33, Line 58 (Expression 85), "k_J" should be changed to -- $y_J$ --.

Column 33, Line 58 (Expression 85), delete " $\dfrac{dk}{dk_{z=}}$ ".

Column 33, Line 60 (Expression 85), insert -- $\dfrac{dk}{dk_{z=}}$ --.

In the Claims

Column 45, Claim 2, Line 44 (third line of Expression C), "$k_x^2$" should be changed to -- $-k_x^2$ --.

Column 47, Claim 6, Line 9 (third line of Expression A), "$k_x^2\}$" should be changed to -- $-k_x^2\}z$ --.

Column 49, Claim 9, Line 8 (third line of Expression C), "$k_x^2$" should be changed to -- $-k_x^2$ --.

Column 51, Claim 14, Line 8 (third line of Expression A), please replace "$a_\theta$" with -- $a$ --.

Column 51, Claim 14, Line 8 (third line of Expression A), "$k_x^2$" should be changed to -- $-k_x^2$ --.